(12) United States Patent
Schaper et al.

(10) Patent No.: US 6,300,333 B1
(45) Date of Patent: Oct. 9, 2001

(54) SUBSTITUTED PIPERIDINES, PROCESSES FOR THEIR PREPARATION AND THEIR USE AS PESTICIDES AND FUNGICIDES

(75) Inventors: Wolfgang Schaper, Diedorf; Ralf Braun, Büttelborn; Harald Jakobi, Frankfurt; Gerhard Krautstrunk, Bad Vilbel; Martin Märkl, Frankfurt; Oswald Ort, Glashütten; Manfred Kern, Lörzweiler; Ulrich Sanft, Hofheim; Werner Bonin, Kelkheim, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/285,199

(22) Filed: Apr. 1, 1999

(30) Foreign Application Priority Data

Apr. 3, 1998 (DE) .............................. 198 15 026

(51) Int. Cl.[7] ..................... A61K 31/505; A61K 31/445
(52) U.S. Cl. ................... 514/256; 514/259; 514/269; 514/315; 514/318
(58) Field of Search ................... 514/256, 259, 514/269, 277, 315, 317–322, 311–314

(56) References Cited

U.S. PATENT DOCUMENTS

| | | |
|---|---|---|
| 5,411,971 | 5/1995 | Edmonds-Alt et al. . |
| 5,567,711 | 10/1996 | Sheppard et al. . |
| 5,571,815 * | 11/1996 | Schaper et al. ............... 514/269 |
| 5,786,371 | 7/1998 | Tsaklakidis et al. . |

FOREIGN PATENT DOCUMENTS

| | | |
|---|---|---|
| 42 08 254 | 9/1993 | (DE) . |
| 43 08 014 | 5/1994 | (DE) . |
| 43 43 250 | 6/1995 | (DE) . |
| 195 04367 | 8/1996 | (DE) . |
| 0191603 | 8/1986 | (EP) . |
| 0515240 | 11/1992 | (EP) . |
| 0522606 | 1/1993 | (EP) . |
| WO 92/17452 | 10/1992 | (WO) . |
| WO 96/37473 | 11/1996 | (WO) . |
| 97/37991 * | 10/1997 | (WO) .................. C07D/405/12 |

* cited by examiner

Primary Examiner—Russell Travers
Assistant Examiner—Shengjun Wang
(74) Attorney, Agent, or Firm—Frommer Lawrence & Haug LLP

(57) ABSTRACT

Substituted piperidines, processes for their preparation and their use as pesticides and fungicides.

The invention relates to substituted piperidines of the formula

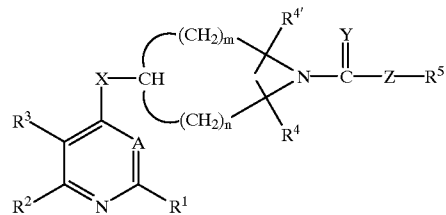

in which
$R^1$ is H, halogen, alkyl, haloalkyl or cycloalkyl;
$R^2$ and $R^3$ are as defined in the description;
A is CH or N;
X is NH, O or $S(O)_q$ where q=0, 1 or 2;
Y and Z are O, S or optionally substituted imino;
m and n are 1, 2, 3, 4 or 5;
$R^4$ and $R^{4'}$ are H, alkyl, haloalkyl, halogen or alkoxy;
$R^5$ is optionally substituted alkyl, alkenyl, alkynyl, aryl or heterocyclyl in which one or more carbon units can be replaced by CO or by hetero atom units;
to processes for their preparation, to compositions comprising them and to their use as pesticides and fungicides.

16 Claims, No Drawings

SUBSTITUTED PIPERIDINES, PROCESSES FOR THEIR PREPARATION AND THEIR USE AS PESTICIDES AND FUNGICIDES

DESCRIPTION

Substituted piperidines, processes for their preparation and their use as pesticides and fungicides.

The invention relates to substituted piperidines, to processes for their preparation and to their use as pesticides and fungicides.

It has already been disclosed that certain 4-(piperidin-4-ylamino)-pyrimidines have fungicidal, acaricidal and insecticidal activity (DE-A42 08 254). However, the biological action of these compounds is not always satisfactory in all exemplary applications, in particular when low application rates and concentrations are used.

There have been found (piperidin-4-ylamino) heterocycles of the formula (I)

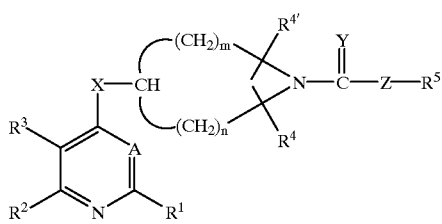

in which the radicals and groups are as defined below and which are highly suitable for controlling animal pests such as insects, arachnids, nematodes, helminth and mollusks, for controlling endoparasites and ectoparasites in the veterinary medicine field and for controlling harmful fungi, while being well tolerated by plants and having favorable toxicity to warm-blooded species.

The invention therefore relates to compounds of the formula (I) in which $R^1$ is hydrogen, halogen, $(C_1-C_8)$-alkyl, $(C_1-C_8)$-haloalkyl, $(C_1-C_8)$-alkoxy or $(C_3-C_6)$-cycloalkyl;

$R^2$ and $R^3$ are identical or different and in each case are hydrogen, $(C_1-C_8)$-alkyl, $(C_2-C_8)$-alkenyl, $(C_2-C_8)$-alkynyl, $(C_1-C_8)$-alkoxy, halogen, hydroxyl, cyano, nitro, thiocyano, $(C_1-C_8)$-alkanoyl, $(C_1-C_8)$-alkoxycarbonyl, $(C_1-C_8)$-alkylthio, $(C_1-C_8)$-alkylsulfinyl, $(C_1-C_8)$-alkylsulfonyl, amino, $(C_1-C_8)$-alkylamino, $(C_1-C_8)$-dialkylamino or $(C_3-C_6)$-cycloalkyl, it being possible for a saturated carbon unit in the alkyl, cycloalkyl, alkenyl and alkynyl radicals or the groups derived from these, such as the alkoxy, alkylthio, alkanoyl, alkoxycarbonyl, alkylthio, alkylsulfinyl, alkylsulfonyl, alkylamino or dialkylamino, to be replaced by a hetero atom unit such as oxygen, $S(O)_x$, where x=0, 1 or 2 or dimethylsilyl, and it furthermore being possible for up to three hydrogen atoms in these radicals or in the groups derived from these to be replaced by halogen, in the case of fluorine it also being possible for all hydrogen atoms to be replaced by fluorine; or $R^2$ and $R^3$ together with the carbon atoms to which they are bonded form an unsaturated 5- or 6-membered isocyclic ring which, if it is a 5-membered ring, may contain an oxygen or sulfur atom in place of $CH_2$ or which, if it is a 6-membered ring, may contain one or two nitrogen atoms in place of one or two CH units and which is optionally substituted by 1, 2 or 3 identical or different radicals and these radicals are $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$ together with the carbon atoms to which they are bonded form a saturated 5-, 6- or 7-membered isocyclic ring which may contain oxygen and/or sulfur in place of one or two $CH_2$ groups and which is optionally substituted by 1, 2 or 3 $(C_1-C_4)$-alkyl groups;

A is CH or N;

X is NH, oxygen or $S(O)_q$ where q=0, 1 or 2;

Y and Z are identical or different and are in each case oxygen, sulfur or a group $NR^{5'}$ or $NR^{5''}$ where $R^{5'}$ and $R^{5''}$ are identical or different and in each case have the meanings given hereinbelow for $R^5$; or, in the event that Y is sulfur or a group $NR^{5'}$, Z may also be a direct bond, or, in the event that Y is a group $NR^{5'}$, $R^{5'}$ may additionally also be nitro, cyano, hydroxyl, alkoxy or a group $NR^{5'''}R^{5''''}$ where $R^{5'''}$ and $R^{5''''}$ are identical or different and in each case may have the meanings given hereinbelow for $R^5$, m and n are identical or different and are the numbers 1, 2, 3, 4 or 5 and the total of m and n does not exceed the number 6;

$R^4$ and $R^{4'}$ are identical or different and are in each case hydrogen, $(C_1-C_4)$-alkyl, $(C_1-C_4)$-haloalkyl, halogen or $(C_1-C_4)$-alkoxy;

$R^5$ is alkyl, alkenyl, alkynyl, aryl, heterocyclyl, it being possible for the aryl or heterocyclyl radicals mentioned to be unsubstituted or to have attached to them up to three, in the case of fluorine also up to the maximum number of, identical or different radicals, and it being possible, in the alkyl, alkenyl or alkynyl radicals mentioned, for one or more, preferably up to three, non-adjacent saturated carbon units to be replaced by a carbonyl group or by hetero atom units such as oxygen, $S(O)_x$, where x=0, 1 or 2, $NR^6$ or $SiR^7R^8$, $R^6$ being hydrogen, $(C_1-C_4)$-alkyl, $(C_1-C_4)$-alkoxy or $(C_1-C_4)$-alkanoyl and $R^7$ and $R^8$ being $(C_1-C_4)$-alkyl, preferably methyl;

and in which, in addition, 3 to 12 atoms of these hydrocarbon radicals which are optionally modified as above may form a cycle;

and it being possible for these hydrocarbon radicals, with or without the abovementioned variations, optionally to be substituted by one or more, preferably up to three, in the case of fluorine up to the maximum number of, identical or different radicals selected from the group consisting of halogen, aryl, aryloxy, arylthio, cycloalkyl, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, halogenalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents, and it furthermore being possible, in the event that Y is a group $NR^{5'}$, $R^{5'}$ of group Y and $R^5$ of group Z to be linked to form a 5–8-membered heteroaliphatic ring system; or it being possible, in the event that Z is a group $NR^{5"}$, for $R^{5"}$ and $R^5$¹ to be linked cyclically to form a 3–8-membered ring system and it being possible for one saturated carbon unit in this ring system to be replaced by oxygen, sulfur or a group NG in which G is an optionally substituted phenyl group, $(C_1-C_4)$-alkyl, $(C_1-C_4)$-alkanoyl or $(C_1-C_4)$-alkoxycarbonyl and it being possible for this ring system to be optionally benzo-fused, and their tautomers and salts, preferably acid addition salts;

in particular those compounds where $R^1$ is hydrogen, halogen, $(C_1-C_4)$-alkyl, $(C_1-C_4)$-haloalkyl or $(C_3-C_5)$-cycloalkyl; $R^2$ and $R^3$ are identical or different in each case are hydrogen; $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, trimethylsilylalkynyl, $(C_1-C_4)$-alkoxy, $(C_1-C_4)$ haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$haloalkanoyl, $(C_3-C_5)$-cycloal kyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, amino, $(C_1-C_4)$-alkylamino or $(C_1-C_4)$-dialkylamino; or $R^2$ and $R^3$ together with the carbon atoms to which they are bonded form an unsaturated 5- or 6-membered isocyclic ring which, if it is a 5-membered ring, may contain an oxygen or sulfur atom in place of $CH_2$ or which, if it is a 6-membered ring, may contain one or two nitrogen atoms in place of one or two CH units and which is optionally substituted by 1, 2 or 3 identical or different radicals, these radicals preferably being $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$ together with the carbon atoms to which they are bonded form a saturated 5-, 6- or 7-membered isocyclic ring which may contain oxygen and/or sulfur in place of one or two $CH_2$ groups and which is optionally substituted by 1, 2 or 3 $(C_1-C_4)$-alkyl groups, and $R^5$ is $(C_1-C_{20})$-alkyl, $(C_2-C_{20})$-alkenyl, $(C_2-C_{20})$-alkynyl, aryl or heterocyclyl, it being possible for the aryl or heterocyclyl radicals mentioned to be unsubstituted or to have attached to them up to three, in the case of fluorine also up to the maximum number of, identical or different radicals and it being possible, in the alkyl, alkenyl or alkynyl radicals mentioned, for one or more, preferably up to three, nonadjacent saturated carbon units to be replaced by a carbonyl group or by hetero atom units such as oxygen, $S(O)_x$ where x=0, 1 or 2, $NR^6$ or $SiR^7R^8$, $R^6$ being hydrogen, $(C_1-C_4)$-alkyl, $(C_1-C_4)$-alkoxy or $(C_1-C_4)$-alkanoyl and $R^7$ and $R^8$ being $(C_1-C_4)$-alkyl, preferably methyl, and in which, moreover, 3 to 12 atoms of these hydrocarbon radicals which are optionally modified as above can form a cycle and it being possible for these hydrocarbon radicals, with or without the variations mentioned, to be optionally substituted by one or more, preferably up to three, in the case of halogen up to the maximum number of, identical or different radicals selected from the group consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_{12})$-alkanoyl, $(C_3-C_8)$-cycloalkanoyl, $(C_2-C_{12})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cylcoalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, Aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents.

Preferred compounds of the formula (I) are those in which $R^1$ is hydrogen, fluorine, chlorine or methyl;

$R^2$ is $(C_1-C_4)$-alkyl, $(C_1-C_4)$-alkenyl, $(C_1-C_4$-alkynyl, $(C_1-C_4)$-haloalkyl, methoxymethyl or cyano;

$R^3$ is hydrogen, halogen, methyl, ethyl, ethynyl, vinyl, halovinyl, $(C_1-C_2)$-fluoroalkyl, methoxy, ethoxy or cyano; or $R^2$ and $R^3$ together with the carbon atoms to which they are bonded form an optionally substituted unsaturated 5- or 6-membered ring which, in the case of the 5-membered ring, may contain a sulfur atom in place of a $CH_2$ unit; or $R^2$ and $R^3$ together with the carbon atoms to which they are bonded form a saturated 5- or 6-membered ring which may contain a sulfur or an oxygen atom in place of a $CH_2$ unit;

A is CH or N;

X is NH or oxygen;

Y and Z are identical or different and are in each case oxygen, sulfur or a group $NR^{5'}$ or $NR^{5"}$;

$R^4$ and $R^{4'}$ are identical or different and are in each case hydrogen or methyl;

m and n are in each case the number 2;

in particular those compounds in which $R^1$ is hydrogen;

$R^2$ is methyl, ethyl, propyl, isopropyl, $(C_1-C_2)$-fluoroalkyl, cyclopropyl or methoxymethyl;

$R^3$ is halogen, methyl, ethyl, ethynyl, vinyl, fluorovinyl, methoxy, ethoxy or cyano; or $R^2$ and $R^3$ together with the ring system to which they are bonded form the quinazoline or quinoline system which may be substituted by fluorine in the carbocyclic moiety; or $R^2$ and $R^3$ together with the carbon atoms to which they are bonded form a saturated 6-membered ring which may contain an oxygen or sulfur atom in place of a $CH_2$ group; and $R^4$ and $R^{4'}$ are hydrogen.

Especially preferred are those compounds of the formula (I), in which $R^1$ is hydrogen;

$R^2$ is methyl, ethyl, propyl, isopropyl, 1-fluoroethyl or methoxymethyl;

$R^3$ is fluorine, chlorine, bromine, cyano, vinyl, ethynyl or methoxy; or, in the event that A is nitrogen, $R^2$ and $R^3$ together with the ring system to which they are bonded form the quinazoline system which may be substituted by a fluorine atom;

A is N;

X is NH;

Y and Z are oxygen or sulfur;

$R^4$ and $R^4$ are hydrogen; and m and n are the number 2.

Most preferred are those compounds of the formula (I) in which $R^1$ is hydrogen;

$R^2$ is ethyl or methoxymethyl;

$R^3$ is fluorine, chlorine, bromine, ethynyl or methoxy, preferably fluorine, chlorine, bromine or methoxy;

A is N;

X is NH;

Y and Z are oxygen or sulfur, preferably oxygen;

$R^4$ and $R^4$ are hydrogen;

m and n are the number 2;

$R^5$ is $(C_1-C_{20})$-alkyl, $(C_2-C_{20})$-alkenyl, $(C_2-C_{20})$-alkynyl, aryl or heterocyclyl, it being possible for the aryl or heterocyclyl radicals mentioned to be unsubstituted or having attached to them up to three, in the case of fluorine also up to the maximum number of, identical or different radicals and it being possible, in the alkyl, alkenyl or alkynyl radicals mentioned, for one or more, preferably up to three, non-adjacent saturated carbon units to be replaced by hetero atom units such as oxygen or $SiR^7R^8$, $R^7$ and $R^8$ being $(C_1-C_4)$-alkyl, preferably methyl, and in which, moreover, 3 to 6 atoms of these hydrocarbon radicals which are optionally modified as above may form a cycle and these hydrocarbon radicals, with or without the variations mentioned, may optionally be substituted by one or more, preferably up to three, in the case of halogen up to the maximum number of, identical or different radicals selected from the group consisting of halogen, preferably fluorine, aryl, aryloxy, arylthio, $(C_3-C_8)$-cycloalkoxy, $(C_3-C_8)$-cycloalkylthio, heterocyclyl, heterocyclyloxy or $(C_1-C_2)$-alkoxycarbonyl, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents;

in particular those compounds where $R^5$ is $(C_1-C_{15})$-alkyl, aryl or heterocyclyl in the sense of a heteroaromatic ring system, it being possible for the aryl or heterocyclyl radical to be unsubstituted or to have attached to it up to three, in the case of fluorine also up to the maximum number of, identical or different radicals and it being possible, in the alkyl radical mentioned, for one or more, preferably up to three, non-adjacent saturated carbon units to be replaced by oxygen, and in which, moreover, 3 to 8 atoms of this alkyl radical which is optionally modified as above may form a cycle and this alkyl radical, with or without the variations mentioned, may optionally be substituted by one or more halogen atoms, in the case of fluorine also up to the maximum number, or with an aryl radical, and this aryl radical may be unsubstituted or have attached to it up to three, in the case of fluorine also up to the maximum number of, identical or different substituents.

In the above formula, "halogen" is understood as meaning a fluorine, chlorine, bromine or iodine atom;

the term "$(C_1-C_4)$-alkyl" an unbranched or branched hydrocarbon radical having 1 to 4 carbon atoms such as, for example, the methyl, ethyl, propyl, isopropyl, 1-butyl, 2-butyl, 2-methylpropyl or tert-butyl radical;

the term "$(C_1-C_8)$-alkyl" the abovementioned alkyl radicals and, for example, the pentyl, 2-methylbutyl, 1,1-dimethylpropyl, hexyl, heptyl, octyl, or the 1,1,3,3-tetramethylbutyl radical;

the term "$(C_1-C_{20})$-alkyl" the abovementioned alkyl radicals and, for example, the nonyl, 1-decyl, 2-decyl, undecyl, dodecyl, pentadecyl or eicosyl radical;

the term "$(C_1-C_4)$-haloalkyl" an alkyl group mentioned under the term $(C_1-C_4)$-alkyl in which one or more hydrogen atoms are replaced by the abovementioned halogen atoms, preferably chlorine or fluorine, such as, for example, the trifluoromethyl group, the 1-fluoroethyl group, the 2,2,2-trifluoroethyl group, the chloromethyl group, the fluoromethyl group, the difluoromethyl group or the 1,1,2,2-tetrafluoroethyl group;

the term "$(C_1-C_2)$-fluoroalkyl", for example, the 1-fluoroethyl, 2-fluoroethyl, 1,1-difluorethyl or the 2,2,2-trifluorethyl group;

the term "cycloalkyl" preferably $(C_3-C_8)$-cycloalkyl;

the term "cycloalkoxy" preferably $(C_3-C_8)$-cycloalkoxy;

the term "cycloalkylthio" preferably $(C_3-C_8)$-cycloalkylthio; the term "$(C_3-C_5)$-cycloalkyl" the cyclopropyl, the cyclobutyl or cyclopentyl group;

the term "$(C_3-C_6)$-cycloalkyl" under the radicals mentioned above under "$(C_3-C_5)$-cycloalkyl", and the cyclohexyl radical;

the term "$(C_3-C_8)$-cycloalkyl" the radicals mentioned above under "$(C_3-C_6)$-cycloalkyl", and the cycloheptyl or cyclooctyl radical;

the term "$(C_3-C_5)$-halocycloalkyl" one of the abovementioned $(C_3-C_5)$-cycloalkyl radicals in which one or more, in the case of fluorine, if appropriate, also all hydrogen atoms, are replaced by halogen, preferably fluorine or chlorine, such as, for example, the 2,2-difluoro or 2,2-dichlorocyclopropane group or the fluorocyclopentane radical;

the term "$(C_2-C_4)$-alkenyl", for example, the vinyl, allyl, 2-methyl-2-propenyl or 2-butenyl group;

the term "$(C_2-C_8)$-alkenyl the abovementioned radicals and, for example, the 1-pentenyl, 2-pentenyl, 3-pentenyl, 4-pentenyl or the 1-octenyl group;

the term "$(C_2-C_{20})$-alkenyl" the abovementioned radicals and, for example, the 2-decenyl or the 2-eicosenyl group;

the term "$(C_2-C_4)$-haloalkenyl" a $(C_2-C_4)$alkenyl group in which some of the hydrogen atoms or, in the case of fluorine, also all of the hydrogen atoms are replaced by halogen, preferably fluorine or chlorine;

the term "$(C_2-C_4)$-alkynyl", for example, the ethynyl, propargyl, 2-methyl-2-propynyl or 2-butynyl group;

the term "$(C_2-C_8)$-alkynyl", for example, the abovementioned radicals and, for example, the 1-pentynyl, 2-pentynyl, 3-pentynyl, 4-pentynyl or the 1-octynyl group, the term "$(C_2-C_{20})$-alkynyl" the abovementioned radicals and, for example, the 1-decynyl or the 2-decynyl group;

the term "$(C_2-C_4)$-haloalkynyl" a $(C_2-C_4)$-alkynyl group in which some of the hydrogen atoms, in the case of fluorine also all of the hydrogen atoms, are replaced by halogen atoms, preferably fluorine or chlorine;

the term "$(C_1-C_4)$-hydroxylalkyl", for example, the hydroxylmethyl, 1-hydroxylethyl, 2-hydroxylethyl, 1-hydroxyl-1-methylethyl or the 1-hydroxylpropyl group;

the term "$(C_1-C_4)$-alkanoyl-$(C_1-C_4)$alkyl", for example, an acetylmethyl, propionylmethyl, 2-acetylethyl or a butyrylmethyl group;

the term "$(C_1–C_4)$-alkanoyl", for example the formyl, acetyl, propionyl, 2-methylpropionyl or butyryl group;

the term $(C_1–C_8)$-alkanoyl the abovementioned radicals and, for example, the valeroyl, pivaloyl, hexanoyl, heptanoyl or octanoyl group; the term "$(C_1–C_{12})$-alkanoyl", for example, the abovementioned radicals and, for example, the nonanoyl, decanoyl or the dodecanoyl group;

the term "$(C_2–C_4)$-haloalkanoyl" a $(C_1–C_4)$-alkanoyl group in which some of the hydrogen atoms, in the case of fluorine also all of the hydrogen atoms, are replaced by halogen atoms, preferably fluorine or chlorine;

the term "$(C_2–C_{12})$-haloalkanoyl" a $(C_1–C_{20})$-alkanoyl group in which some of the hydrogen atoms, in the case of fluorine also all of the hydrogen atoms, are replaced by halogen atoms, preferably fluorine or chlorine;

the term "cyano-$(C_1–C_4)$-alkyl" a cyanoalkyl group whose hydrocarbon radical has the meanings given under the term "$(C_1–C_4)$-alkyl"

the terms "$(C_1–C_4)$-nitroalkyl" or "$(C_1–C_4)$-thiocyanoalkyl" one of the abovementioned $(C_1–C_4)$-alkyl groups which are substituted by a nitro or a thiocyano group;

the term "$(C_1–C_4)$-alkoxycarbonyl", for example, the methoxycarbonyl, ethoxycarbonyl, propoxycarbonyl, butoxycarbonyl or tert-butoxycarbonyl group;

the term "$(C_1–C_8)$-alkoxycarbonyl", for example, the radicals mentioned above, and, for example, the pentyloxycarbonyl, hexyloxycarbonyl or the octyloxycarbonyl group; the term "$(C_1–C_{12})$-alkoxycarbonyl" the radicals mentioned above and, for example, the nonyloxycarbonyl, 2-methyloctyloxycarbonyl, decyloxycarbonyl or dodecyloxycarbonyl group;

the term "$(C_1–C_4)$-alkoxycarbonyl-$(C_1–C_4)$-alkyl", for example, a methoxycarbonylmethyl, ethoxycarbonylmethyl or methoxycarbonylethyl group;

the term "$(C_1–C_4)$-haloalkoxycarbonyl" a $(C_1–C_4)$-alkoxycarbonyl group, in which one or more, in the case of fluorine optionally also all, hydrogen atoms are replaced by halogen, preferably fluorine or chlorine;

the term "$(C_1–C_4)$-alkylthio" an alkylthio group whose hydrocarbon radical has the meaning given under the term "$(C_1–C_4)$-alkyl"; the term "$(C_1–C_8)$-alkylthio" an alkylthio group whose alkyl radical has the meaning given under the term "$(C_1–C_8)$-alkyl";

the term "$(C_1–C_4)$-haloalkylthio" a $(C_1–C_4)$-alkylthio group in which one or more, in the case of fluorine optionally also all, hydrogen atoms of the hydrocarbon moiety are replaced by halogen, in particular chlorine or fluorine;

the term "$(C_1–C_4)$-alkylsulfinyl", for example, the methyl-, ethyl-, propyl-, isopropyl-, butyl-, isobutyl-, sec-butyl- or tert-butylsulfinyl group;

The term "$(C_1–C_8)$-alkylsulfinyl" one of the alkylsulfinyl groups mentioned above and, for example, the pentylsulfinyl, 2-methylbutylsulfinyl, hexylsulfinyl or octylsulfinyl group;

the term "$(C_1–C_4)$-alkylsulfonyl", for example, the methyl-, ethyl-, propyl-, isopropyl-, butyl-, isobutyl-, sec-butyl- or tert-butylsulfonyl group; the terms "$(C_1–C_4)$-haloalkylsulfinyl" and "$(C_1–C_4)$-haloalkylsulfonyl" $(C_1–C_4)$-alkylsulfinyl and -sulfonyl radicals having the abovementioned meanings where one or more, in the case of fluorine optionally also all, hydrogen atoms of the hydrocarbon moiety are replaced by halogen, in particular chlorine or fluorine; the terms "fluoromethylsulfinyl" and "fluoromethylsulfonyl" the mono-, di- and trifluoromethyl-sulfinyl and -sulfonyl group;

the term "$(C_1–C_4)$-alkoxy" an alkoxy group whose hydrocarbon radical has the meaning given under the term "$(C_1–C_4)$-alkyl";

the term "$(C_1–C_8)$-alkoxy" an alkoxy group whose hydrocarbon radical has the meaning given under the term "$(C_1–C_8)$-alkyl";

the term "$(C_1–C_8)$-alkylsulfonyl" one of the alkylsulfonyl groups mentioned above and, for example, the pentyl-, 2-methylbutyl-, hexyl-, heptyl- or octylsulfonyl groups, the term "$(C_1–C_4)$-alkylamino", for example, the methylamino, ethylamino, propylamino, isopropylamino, butylamino, isobutylamino, sec-butylamino or the tert-butylamino group, the term "$(C_1–C_8)$-alkylamino" one of the $(C_1–C_4)$-alkylamino groups mentioned above and, for example, the pentylamino, hexylamino, heptylamino or octylamino group;

the term "$(C_1–C_4)$-dialkylamino", for example, the dimethylamino, methyl-ethylamino, diethylamino, dipropylamino or the dibutylamino group, but also cyclic systems such as, for example, the pyrrolidino or piperidino group, the term "$(C_1–C_8)$-dialkylamino" one of the $(C_1–C_4)$-dialkylamino groups mentioned above and, for example, the dipentyl, dihexyl or the dioctylamino group;

the term "$(C_1–C_4)$-haloalkoxy" a haloalkoxy group whose halohydrocarbon radical has the meaning given under the term "$(C_1–C_4)$-haloalkyl"; the term "$(C_1–C_4)$-alkoxy-$(C_1–C_4)$-alkyl", for example, a 1-methoxyethyl group, a 2-methoxyethyl group, a 2-ethoxyethyl group, a methoxymethyl or ethoxymethyl group, a 3-methoxypropyl group or a 4-butoxybutyl group;

the terms "$(C_1–C_4)$-haloalkoxy-$(C_1–C_4)$-alkyl, "$(C_1–C_4)$-alkoxy-$(C_1–C_4)$-haloalkyl" and "$(C_1–C_4)$-haloalkoxy-$(C_1–C_4)$-haloalkyl" $(C_1–C_4)$-alkoxy-$(C_1–C_4)$-alkyl radicals having the abovementioned meanings where one or more, in the case of fluorine optionally also all, hydrogen atoms of the respective hydrocarbon moieties are replaced by halogen, preferably chlorine or fluorine;

the term "$(C_1–C_4)$-alkylthio-$(C_1–C_4)$-alkyl", for example, methylthiomethyl, ethylthiomethyl, propylthiomethyl, 2-methylthioethyl, 2-ethylthioethyl or 3-methylthiopropyl;

the term "aryl" an isocyclic aromatic radical having preferably 6 to 14, in particular 6 to 12, carbon atoms such as, for example, phenyl, naphthyl or biphenylyl, preferably phenyl;

the term "heterocyclyl" preferably a heteroaromatic or heteroaliphatic ring system, "heteroaromatic ring systems" preferably being understood as meaning an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, quinnoline, 1,8-naphthyridine, 1,5-naphthyridine, 1,6-naphthyridine, 1,7-naphthyridine, phthalazine, pyridopyrimidine, purine, pteridine or 4H-quinolizine; and the term "heteroaliphatic ring system" preferably a $(C_3–C_8)$-cycloalkyl radical in which at least one carbon unit is replaced by O, S or a group $NR^{11}$ and $R^{11}$ is hydrogen, $(C_1–C_4)$-alkyl, $(C_1–C_4)$-alkoxy or aryl;

the term "arylthio", for example, the phenylthio or the 1- or 2-naphthylthio group;

the term "aryloxy", for example, the phenoxy or 1- or 2-naphthyloxy group;

the term "heterocyclyloxy" or "heterocyclylthio" one of the abovementioned heterocyclic radicals which are linked via an oxygen or sulfur atom;

the term "($C_3$–$C_8$)-cycloalkoxy" or "($C_3$–$C_8$)-cycloalkylthio" one of the abovementioned ($C_3$–$C_8$)-cycloalkyl radicals which are linked via an oxygen or sulfur atom;

the term "Aroyl", for example, the benzoyl, naphthoyl or the biphenylcarbonyl group;

the term "aryl-($C_1$–$C_4$-alkanoyl", for example, the phenylacetyl, 3-phenylpropionyl, 2-phenylpropionyl, 2-methyl-2-phenylpropionyl, 4-phenylbutyryl or the naphthylacetyl group;

the term "($C_3$–$C_8$)-cycloalkyl-($C_1$–$C_4$)-alkanoyl", for example, the cyclopropylcarbonyl, cyclobutylcarbonyl, cyclopentylcarbonyl, cyclohexylcarbonyl, cyclohexylacetyl or the cyclohexylbutyryl group;

the term "heterocyclyl-($C_1$–$C_4$)-alkanoyl", for example, the thenoyl, furoyl, nicotinoyl, thienylacetyl or die pyridinepropionyl group;

the term "($C_3$–$C_8$)-cycloalkoxycarbonyl", for example, the cyclobutyloxycarbonyl, cyclopentyloxycarbonyl, cyclohexyloxycarbonyl or the cycloheptyloxycarbonyl group;

the term "($C_3$–$C_8$)-cycloalkyl-($C_1$–$C_4$)-alkoxycarbonyl", for example, the cyclopropylmethoxycarbonyl, cyclobutylmethoxycarbonyl, cyclopentyloxymethoxycarbonyl, cyclohexyloxymethoxycarbonyl, 1-(cyclohexyl)ethoxycarbonyl or the 2-(cyclohexyl)ethoxycarbonyl group;

the term "aryl-($C_1$–$C_4$)-alkoxycarbonyl", for example, the benzyloxycarbonyl, 1-naphthylmethoxycarbonyl, 2-naphthylmethoxycarbonyl, 1-phenylethoxycarbonyl or the 2-phenylethoxycarbonyl group;

the term "heterocyclyl-($C_1$–$C_4$)-alkoxycarbonyl", for example, the thienylmethoxycarbonyl, furylmethoxycarbonyl, tetrahydrofurylmethoxycarbonyl or the pyridylethoxycarbonyl group;

the term "aryloxycarbonyl", for example, the phenoxycarbonyl, naphthoxycarbonyl or the biphenyloxycarbonyl group;

the term "heterocyclyloxycarbonyl", for example, the tetrahydropyran-4-oxycarbonyl group;

the term "($C_1$–$C_{20}$)-alkanoyloxy", for example, the formyloxy, acetoxy, propionyloxy, butyryloxy, pivaloyloxy, valeroyloxy or the hexanoyloxy group; the term "($C_2$–$C_{20}$)-haloalkanoyloxy" a ($C_2$–$C_{20}$)-alkanoyloxy group in which one or more, in the case of fluorine optionally also all, hydrogen atoms of the hydrocarbon moiety are replaced by halogen, in particular fluorine or chlorine;

the term "($C_3$–$C_8$)-cycloalkanoyloxy", for example, the cyclopropanoyloxy, cyclobutenoyloxy, cyclopentanoyloxy, cyclohexanoyloxy or the cycloheptanoyloxy group;

the term "($C_3$–$C_8$)-cycloalkyl-($C_1$–$C_4$)-alkanoyloxy", for example the cyclopropylcarbonyloxy, cyclopropylacetoxy, cyclobutylcarbonyloxy, cyclopentylcarbonyloxy, cyclohexylcarbonyloxy, cyclohexylacetoxy or the 4-cyclohexylbutyryloxy group;

the term "aroyloxy", for example, the benzoyloxy or the naphthoyloxy group;

the term "aryl-($C_1$–$C_4$)-alkanoyloxy", for example, the benzoyloxy, naphthoyloxy, biphenylcarbonyloxy, phenylacetoxy or the phenylbutyryloxy group;

the term "heterocyclyl-($C_1$–$C_4$)-alkanoyloxy", for example, the thienylcarbonyloxy, thienylacetoxy, pyridylcarbonyloxy or the pyrimidinylcarbonyloxy group;

the term "($C_1$–$C_{20}$)-alkylsulfonyloxy", for example, the methane-, ethane-, butane- or hexanesulfonyloxy group;

the term "arylsulfonyloxy", for example, the phenylsulfonyloxy or the toluenesulfonyloxy group;

the term "halovinyl" a vinyl group in which some or all of the hydrogen atoms are replaced by halogen, preferably fluorine or chlorine;

the term "fluorovinyl" a vinyl group in which some or all of the hydrogen atoms are replaced by fluorine.

The substituents which the various aliphatic, cycloaliphatic, aromatic and heterocyclic ring systems can have attached to them include, for example, halogen, nitro, cyano, di-($C_1$–$C_4$)-alkylamino, ($C_1$–$C_4$)-alkyl, ($C_3$–$C_8$)-cycloalkyl, ($C_1$–$C_4$)-trialkylsilyl, ($C_1$–$C_4$)-alkoxy, ($C_1$–$C_4$)-alkoxy-($C_1$–$C_4$)-alkyl, ($C_1$–$C_2$)-alkoxy-[$CH_2CH_2O$]$_{0,1,2}$-ethoxy, ($C_1$–$C_4$)-alkylthio, ($C_1$–$C_4$)-alkylsulfinyl, ($C_1$–$C_4$)-alkylsulfonyl, phenyl, benzyl, phenoxy, halophenoxy, ($C_1$–$C_4$)-alkylphenoxy, ($C_1$–$C_4$)-alkoxyphenoxy, phenylthio, heterocyclyl, heterocylylthio or heterocyclyloxy, it being possible, in the alkyl radicals and the radicals derived from these, for one or more, in the case of fluorine also up to the maximum number of, hydrogen atoms, to be replaced by halogen, preferably chlorine or fluorine, it also being possible, in the event that these substituents are ($C_1$–$C_4$)-alkyl, for them to be cyclically linked and it being possible, in these fused ring systems such as, for example, the indane, di-, tetra- or decahydronaphthyl or benzocycloheptane system, for one or two aliphatic carbon units to be replaced by hetero atom units such as oxygen or sulfur, and it being possible, on the aliphatic carbon atom units, for one or more, in the case of fluorine also up to the maximum number of, hydrogen atoms to be replaced by halogen or ($C_1$–$C_4$)-alkyl.

The definition "it being possible, in the alkyl, alkenyl or alkynyl radicals mentioned, for one or more, preferably up to three, non-adjacent saturated carbon units to be replaced by a carbonyl group or by hetero atom units such as oxygen, $S(O)_x$ where x=0, 1 or 2, $NR^6$ or $SiR^7R^8$, where $R^6$ is hydrogen, ($C_1$–$C_4$)-alkyl, ($C_1$–$C_4$)-alkoxy or ($C_1$–$C_4$)-alkanoyl and $R^7$ and $R^8$ are ($C_1$–$C_4$)-alkyl, preferably methyl, and it furthermore being possible for 3 to 12 atoms of these hydrocarbon radicals which are optionally modified as above to form a cycle and for these hydrocarbon radicals, with or without the abovementioned variations, optionally to be substituted by one or more, preferably up to three, in the case of fluorine up to the maximum number of, identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, Heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents" is to be understood as meaning, for example, alkoxyalkyl radicals such as, for example, the methoxymethyl, methoxyethyl or ethoxyethyl group; or alkoxyalkoxyalkyl radicals such as, for example, the methoxy or the ethoxy-ethoxyethyl group; or alkylthioalkyl radicals such as, for example, the methyl or the ethyl-thioethyl group; or alkylsulfinylalkyl radicals such as, for example, the methyl- or ethyl-sulfinylethyl group; or alkylsulfonylalkyl radicals such as, for example, the methyl- or ethyl-sulfonylethyl group; or alkyldialkylsilylalkyl, preferably alkyldimethylsilylalkyl, radicals, such as, for example, the timethylsilylmethyl or the trimethylsilylethyl group; or trialkylsilyl, preferably alkyldimethylsilyl, radicals such as, for example, the trimethylsilyl, ethyldimethylsilyl, tert-butyidimethylsilyl or the octyldimethylsilyl group; or cycloalkyldialkylsilyl, preferably cycloalkyldimethylsilyl, radicals such as, for example, the cyclohexyldimethylsilyl group; or aryidialkylsilyl, preferably aryldimethylsilyl, radicals such as, for example, the phenyidimethylsilyl group; or arylalkyldialkylsilyl, preferably arylalkyldimethylsilyl, radicals such as, for example, the benzyldimethylsilyl or the phenylethyldimethylsilyl group; or alkanoylalkyl radicals such as, for example, the acetylmethyl or the pivaloylmethyl group;

or cycloalkanoylalkyl radicals such as, for example, the cyclopropylcarbonylmethyl or the cyclohexylcarbonylmethyl group; or haloalkanoylalkyl radicals such as, for example, the trifluoro- or trichloroacetylmethyl group; or aroylalkyl radicals such as, for example, the benzoyl-, or naphthoylalkyl radicals such as, for example, the phenylacetylmethyl group; or heterocyclylcarbonylalkyl radicals such as, for example, the thienyl- or pyridylacetylmethyl group; or arylalkyl radicals such as, for example, the benzyl, the 2-phenylethyl, the 1-phenylethyl, the 1-methyl-1-phenylethyl group, the 3-phenylpropyl group, the 4-phenylbutyl group, the 2-methyl-2-phenylethyl group or the 1-methyl- or 2-methyl-naphthyl group; or heterocyclylalkyl radicals such as, for example, the thienylmethyl, pyridylmethyl, furfuryl, tetrahydrofurfuryl, tetrahydropyranylmethyl or the 1,3-dioxolane-2-methyl group; or aryloxyalkyl radicals such as, for example, the phenoxymethyl or naphthoxymethyl group; or cycloalkyl radicals, either monocyclic such as, for example, the cyclopropyl, cyclobutyl, cyclopentyl, cyclohexyl, cycloheptyl or cyclooctyl radical, bicyclic such as, for example, the norbornyl radical or the bicyclo[2,2,2]octyl radical, or fused, such as the decahydronaphthyl radical;

alkylcycloalkyl radicals such as, for example, the 4-methyl or the 4-tert-butylcyclohexyl group or the 1-methylcyclopropyl, -cyclobutyl, -cyclopentyl or -cyclohexyl group;

cycloalkylalkyl radicals such as, for example, the cyclohexylmethyl or -ethyl group;

cycloalkylene radicals, either monocyclic, such as, for example, the cyclopentenyl, cyclohexenyl, cycloheptenyl or cyclooctenyl radical, bicyclic, such as, for example, the norbornenyl or the bicyclo[2,2,2]octenyl radical, or fused such as the various dihydro- or tetrahydronaphthyl radicals;

cycloalkylenealkyl radicals such as, for example, the 1-cyclohexenylmethyl or -ethyl radical;

or else haloalkyl derivatives of the corresponding groups such as, for example, haloalkyl, haloalkoxyalkyl, alkoxyhaloalkyl, haloalkylcycloalkyl or halocycloalkyl radicals.

The explanation given above applies correspondingly to homologs or radicals derived from them.

The present invention relates to compounds of the formula (I) in the form of the free base or of an acid addition salt. Acids which can be used for salt formation are inorganic acids such as hydrochloric acid, hydrobromic acid, nitric acid, sulfuric acid, phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula (I) have one or more asymmetric carbon atoms or stereoisomers on double bonds. Enantiomers or diastereomers may therefore occur. The invention extends not only to the pure isomers but also to mixtures of these. The diastereomer mixtures can be resolved into the components by customary methods, for example by selective crystallization from suitable solvents or by chromatography. Racemates can be resolved by customary methods to give the enantiomers, for example by salt formation with a chiral enantiomerically pure acid, separation of the diastereomeric salts and liberation of the pure enantiomers by means of a base.

The invention furthermore relates to a process for the preparation of compounds of the formula (I) which comprises reacting a compound of the formula (II)

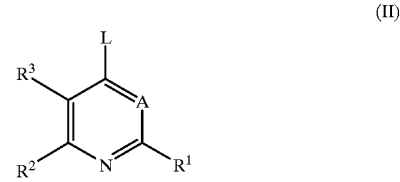

(II)

in which A, $R^1$, $R^2$ and $R^3$ have the meanings given in formula I and L is a leaving group, for example halogen, alkylthio, alkanesulfonyloxy or arylsulfonyloxy, alkylsulfonyl or arylsulfonyl, with a nucleophile of the formula (III)

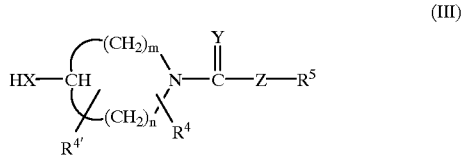

(III)

in which X, Y, Z, m, n, $R^4$, $R^{4'}$ and $R^5$ have the meanings given above under formula I and optionally derivatizing further the pyridine or pyrimidine system or the piperidine side chain in the compounds of the formula (I) obtained thus or in another manner and optionally converting the resulting compounds into their salts.

The substitution reaction described above is known in principle. The leaving group L can be varied within wide limits and may be, for example, a halogen atom, such as fluorine, chlorine, bromine or iodine, or alkylthio, such as methyl- or ethylthio, or alkanesulfonyloxy, such as methane-, trifluoromethane- or ethanesulfonyloxy, or arylsulfonyloxy, such as benzenesulfonyloxy or toluenesulfonyloxy, or alkylsulfonyl, such as methyl- or ethylsulfonyl, or arylsulfonyl, such as phenyl- or toluenesulfonyl.

The abovementioned reaction is carried out in a temperature range of 20 to 1 50° C., expediently in the presence of a base and, if appropriate, in an inert organic solvent such as N,N-dimethylformamide, N,N-dimethylacetamide, dimethylsulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the above-mentioned solvents may also be used.

In the event that X is oxygen, examples of suitable bases are carbonates, hydrogen carbonates, amides or hydrides of alkali metal or alkaline earth metals, such as sodium carbonate, sodium hydrogen carbonate, potassium carbonate, sodium amide or sodium hydride, and in the event that X is NH, examples of suitable bases are carbonates, hydrogen carbonates, hydroxides, amides or hydrides of alkali metals or alkaline earth metals, such as sodium carbonate, sodium hydrogen carbonate, potassium carbonate, sodium hydroxide, sodium amide or sodium hydride, or organic bases such as triethylamine or pyridine. A second equivalent of an amine of the formula (III) may also be employed as auxiliary base.

The compounds of the formula (II) required as starting materials are known from the literature in most cases or may be prepared analogously to known methods (cf., for example, EP-A 0 370 391, EP-A 0 470 600, DE-A43 31 179, DE-A44 04 702).

To prepare the nucleophiles of the formula (III), suitably substituted compounds of the formula (IV)

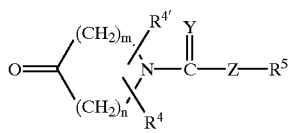

(IV)

are preferably used as starting materials, and they are converted into the corresponding amines by reductive amination (H$_2$, NH$_3$, metal catalyst or ammonium acetate/sodium cyanoborohydride or Leuckart-Wallach reduction) or into the corresponding alcohols by reduction with a complex metal hydride.

Starting compounds of the formula (IV) are known in some cases or can be prepared analogously to known processes.

The invention furthermore relates to a process for the preparation of compounds of the formula (I) which comprises reacting a compound of the formula (II)

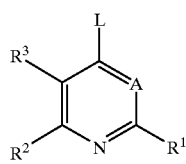

(II)

in which A, R$^1$, R$^2$ and R$^3$ have the meanings given under formula (I) and L is a leaving group, for example halogen, alkylthio, alkanesulfonyloxy or arylsulfonyloxy, alkylsulfonyl or arylsulfonyl, with a nucleophile of the formula (V)

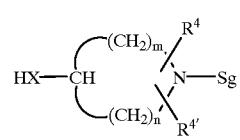

(V)

in which X, R$^4$, R$^{4'}$, m and n have the meanings given under formula (I) and Sg is a protective group, eliminating, in the resulting compounds of the formula (VI)

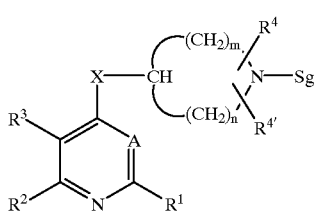

(VI)

in which A, R$^1$, R$^2$, R$^3$, X, m, n, R$^4$ and R$^{4'}$ have the meanings given under formula (I) and Sg is a protective group, the protective group Sg and reacting the resulting compound of the formula (VII)

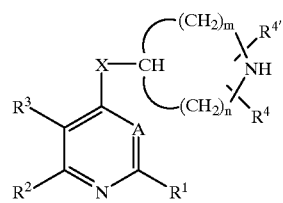

(VII)

in which R$^1$, R$^2$ R$^3$, A, X, m, n, R$^4$ and R$^{4'}$ have the meanings given above under formula (I) with a compound of the formula (VIII)

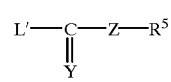

(VIII)

in which Y, Z and R$^5$ have the meanings indicated for formula (I) and L' is a leaving group, preferably fluorine, chlorine or bromine, and optionally further derivatizing the pyridine or pyrimidine system or the piperidine side chain in the compounds of the formula (I) which have been obtained thus or in another manner.

Examples of suitable protective groups Sg for formula VI are the trifluoroacetyl, tert-butoxycarbonyl, benzyloxycarbonyl, benzyl, methoxybenzyl, dimethoxybenzyl, trityl or the 9-phenylfluorenyl group, each of which can be eliminated under basic, acidic, hydrogenolytic or oxidative conditions (cf., for example, P. J. Kocienski, Protecting Groups, Georg Thieme Verlag, Stuttgart 1994).

The reaction of the compounds of the formula (II) with the compounds of the formula (V) to give the compounds of the formula (VI) is totally analogous to the reaction of the compounds of the formula (II) with the compounds of the formula (III).

The protective group Sg is elminated from the compounds of the formula (VI) for example by the methods given in the literature for the individual protective groups (cf., for example, P. J. Kocienski, Protecting Groups, Georg Thieme Verlag, Stuttgart 1994). Thus, a tert-butoxycarbonyl protective group is eliminated by treating the compound of formula (VI) with acid in an inert solvent such as, for example, dichloromethane or toluene.

The reaction of the compounds of the formula (VII) with the compounds of the formula VII to give the end product of the formula (I) is expediently carried out in the presence of a base such as, for example, triethylamine or pyridine, or in the presence of inorganic acid binders such as, for example, alkali carbonates, alkaline earth metal carbonates, alkali hydrogen carbonates or alkaline earth metal hydrogen carbonates such as, for example, sodium carbonate, potassium carbonate, calcium carbonate, sodium hydrogen carbonate or potassium hydrogen carbonate, in an inert solvent such as, for example, dichloromethane, trichloromethane, tetrahydrofuran, benzene, toluene or pyridine.

Those compounds of the formula (V) and of the formula (VIII) which are not already known can be prepared analogously to known processes.

The intermediates of the formula (VII) are novel and also part of the invention.

Collections of compounds of the formula (I) which can be synthesized in accordance with the abovementioned scheme may also be prepared in parallel, which may be effected by the manual, semiautomated or fully automated route. It is possible to automate carrying out the reaction or working up or purifying of the products or intermediates. In total, this is to be understood as a procedure as described, for example, by S. H. DeWitt in "Annual Reports in Combinatorial Chemistry and Molecular Diversity: Automated synthesis", Volume 1, Verlag Escom 1997, pages 69 to 77.

A series of commercially available apparatuses as they are available from, for example, Stem Corporation, Woodrolfe Road, Tollesbury, Essex, CM9 8SE, England or H+P Labortechnik GmbH, Bruckmannring 28, 85764 Oberschleilheim, Germany, may be used for carrying out the reaction and for working-up in parallel. Equipment which are available for the parallel purification of compounds of the formula (I) or of intermediate obtained on preparation are, inter alia, chromatography apparatuses, for example those of ISCO, Inc., 4700 Superior Street, Lincoln, Nebr. 68504, USA.

The apparatuses mentioned lead to a modular procedure in which the individual process steps are automated, but manual operations must be carried out between the process steps. This may be avoided by employing partially or fully integrated automation systems in which the automation modules in question are operated, for example, by robots. Such automation systems can be obtained, for example, from Zymark Corporation, Zymark Center, Hopkinton, Mass. 01748, USA.

In addition to the procedure described here, the compounds of the formula (I) may be prepared entirely or partially by solid-phase techniques. To this end, individual intermediates or all intermediates of the synthesis or of a synthesis adapted to suit the relevant procedure are bound to a synthetic resin. Solid-phase synthetic techniques are described sufficiently in the specialist literature, for example Barry A. Bunin in "The Combinatorial Index", Academic Press, 1998.

The use of solid-phase synthetic methods permits the use of a series of protocols known from the literature which, in turn, can be carried out manually or in an automated fashion.

For example, the "Tea-bag method" (Houghten, US 4,631, 211; Houghten et al., Proc. Natl. Acad. Sci, 1985, 82, 5131–5135), in which products of IRORI, 11149 North Torrey Pines Road, La Jolla, Calif. 92037, USA, are employed, may be partially automated. The automation of solid-phase parallel syntheses is carried out successfully for example using apparatuses of Argonaut Technologies, Inc., 887 Industrial Road, San Carlos, Calif. 94070, USA or MultiSynTech GmbH, Wullener Feld 4, 58454 Witten, Germany.

The preparation in accordance with the processes described herein yields compounds of the formula (I) in the form of substance collections termed libraries. The present invention also relates to libraries containing at least two compounds of the formula (I). The active substances of the formula (I) are well tolerated by plants, show favorable toxicity to warm-blooded species and are suitable for controlling animal pests, in particular insects, arachnids, helminths and mollusks, very particularly preferably for controlling insects and arachnids which occur in agriculture, in livestock husbandry, in forests, in the protection of stored products and materials, and in the hygiene sector. They are active against normally sensitive and resistant species and against all or individual developmental stages. The above-mentioned pests include:

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp., Eutetranychus spp.

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrlx viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon soistitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus, Latrodectus mactans*.

From the class of the helminths, for example, Haemonchus, Trichostrongulus, Ostertagia, Cooperia, Chabertia, Strongyloides, Oesophagostomum, Hyostrongulus, Ancylostoma, Ascaris, Heterakis and Fasciola.

From the class of the gastropods, for example, Deroceras spp., Arion spp., Lymnaea spp., Galba spp., Succinea spp., Biomphalaria spp., Bulinus spp., Oncomelania spp.

From the class of the bivalves, for example, Dreissena spp.

The plant-parasitic nematodes which can be controlled in accordance with the invention include, for example, the root-parasitic soil nematodes such as, for example, those of the genera Meloidogyne (root gall nematodes such as *Meloidogyne incognita, Meloidogyne hapla* and *Meloidogyne javanica*), Heterodera and Globodera (cyst-nematodes such as *Globodera rostochiensis, Globodera pallida, Heterodera trifolii*) and of the genera Radopholus such as *Radopholus similis*, Pratylenchus such as *Pratyglenchus neglectus, Pratylenchus penetrans* and *Pratylenchus curvitatus;*

Tylenchulus such as *Tylenchulus semipenetrans*, Tylenchorhynchus, such as *Tylenchorhynchus dubius* and *Tylenchorhynchus claytoni*, Rotylenchus such as *Rotylenchus robustus*, Heliocotylenchus such as *Haliocotylenchus multicinctus*, Belonoaimus such as *Belonoaimus longicaudatus*, Longidorus such as *Longidorus elongatus*, Trichodorus such as *Trichodorus primitivus* and Xiphinema such as *Xiphinema index*.

The compounds according to the invention are also suitable for controlling the nematode genera Ditylenchus (stem parasites, such as *Ditylenchus dipsaci* and *Ditylenchus destructor*), Aphelenchoides (foliar nematodes, such as *Aphelenchoides ritzemabosi*) and Anguina (seed nematodes, such as *Anguina tritici*).

The invention also relates to compositions, in particular insecticidal and acaricidal compositions, which comprise the compounds of the formula (I) in addition to suitable formulation auxiliaries.

The compositions according to the invention generally comprise 1 to 95% by weight of the active substances of the formula (1).

They may be formulated in various ways, depending on the prevailing biological and/or chemical-physical parameters. Possible formulations which are preferably suitable are:

wettable powders (WP), emulsifiable concentrates (EC), aqueous solutions (SL), emulsions, sprayable solutions, oil- or water-based dispersions (SC), suspoemulsions (SE), dusts (DP), seed-dressing materials, granules in the form of microgranules, spray granules, coated granules and adsorption granules, water-dispersible granules (WG), ULV formulations, microcapsules, waxes or baits.

These individual types of formulation are known in principle and described, for example, in:

Winnacker-Küchler, "Chemische Technologie" [Chemical Technology], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives, are also known and described, for example, in Watkins, "Handbook of Insecticide Dust Diluents and Garriers", 2nd Ed., Darland Books, Caldwell N.J.; H. v. Olphen, "Introduction to Clay Colloid Chemistry", 2nd .40 Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schbnfeldt, "Grenzflächenaktive Äthylenoxidaddukte" [Surface-active ethylene oxide adducts] Wiss. Verlagsgesell., Stuttgart 1967; Winnacker-Küchler, "Chemische Technologie", Volume 7, C. HauserVerlag Munich, 4th Ed. 1986.

Based on these formulations, it is also possible to prepare combinations with other pesticidally active substances, fertilizers and/or growth regulators, for example in the form of a readymix or a tank mix. Wettable powders are products which are uniformly dispersible in water and which, besides the active substance, additionally comprise wetters, for example, polyoxethylated alkylphenols, polyoxyethylated fatty alcohols, alkyl- or alkylphenolsulfonates and dispersants, for example sodium lignosulfonate or sodium 2,2'-dinaphthylmethane-6,6'-disulfonate, in addition to a diluent or inert substance.

Emulsifiable concentrates are prepared by dissolving the active substance in an organic solvent, for example butanol, cyclohexanone, dimethylformamide, xylene, or else high-boiling aromatics or hydrocarbons, with addition of one or more emulsifiers. The following are examples of emulsifiers which can be used: calcium alkylarylsulfonates such as calcium dodecylbenzenesulfonate, or non-ionic emulsifiers such as fatty acid polyglycol esters, alkylaryl polyglycol ethers, fatty alcohol polyglycol ethers, propylene oxide/ ethylene oxide condensates, alkyl polyethers, sorbitan fatty acid esters, polyoxyethylene sorbitan fatty acid esters or polyoxyethylene sorbitol esters.

Dusts are obtained by grinding the active substance with finely divided solid materials, for example talc, natural clays such as kaolin, bentonite, pyrophyllite, or diatomaceous earth. Granules can be prepared either by spraying the active substance onto adsorptive granulated inert material or by applying active substance concentrates to the surface of carriers such as sand, kaolinites or granulated inert material with the aid of binders, for example polyvinyl alcohol, sodium polyacrylate or else mineral oils. Suitable active substances may also be granulated in the manner conventionally used for the preparation of fertilizer granules, if desired as a mixture with fertilizers.

The active substance concentration in wettable powders is, for example, approximately 10 to 90% by weight, the remainder to 100% being composed of customary formulation components. In the case of emulsifiable concentrates, the active substance concentration can be approximately 5 to 80% by weight. Formulations in the form of dust usually comprise 5 to 20% by weight of active substance, sprayable solutions approximately 2 to 20% by weight. In the case of granules, the active substance content depends partly on whether the active compound is in liquid or solid form and on which granulation auxiliaries, fillers and the like are used.

In addition, the active substance formulations mentioned optionally comprise the adhesives, wetters, dispersants, emulsifiers, penetrants, solvents, fillers or carriers which are conventional in each case.

For use, the concentrates, which are in commercially available form, are optionally diluted in the customary manner, for example using water in the case of wettable powders, emulsifiable concentrates, dispersions and in some cases also microgranules. Preparations in the form of dusts, granulated preparations and sprayable solutions are usually not diluted further with other inert substances prior to use.

The application rate required varies with the external conditions such as, inter alia, temperature and humidity. It may vary within wide limits, for example, between 0.0005 and 10.0 kg/ha or more of active ingredient, but it is preferably between 0.001 and 5 kg/ha.

The active substances according to the invention may be present in their commercially available formulations, and in the application forms prepared from these formulations, alone or as a mixture with other active substances, such as insecticides, attractants, sterilants, acaricides, nematicides, fungicides, growth regulators or herbicides.

The pesticides with which the compounds of the formula (I) can be combined include, for example, phosphoric esters, carbamates, carboxylates, formamidines, tin compounds and substances produced by micro-organisms, inter alia.

Preferred components in mixture are 1. from the group comprising the phosphorus compounds acephate, azamethiphos, azinphos-ethyl, azinphosethyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulphone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824) heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, primiphos-ethyl, pirimiphos-methyl, profenofos, propaphos, proetamphos, prothiofos, pyraclofos, pyridapenthion, quinalphos, suiprofos, temephos, terbufos, tebupirimfos, tetrachlorvinphos, thiometon, triazophos, trichlorphon, vamidothion;

2. from the group comprising the carbamates alanycarb (OK-135), aldicarb, 2-sec-butylphenylmethylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl (methyl)carbamate, oxamyl, pirimicarb, propoxur, thiodicarb, thiofanox, 1-methylthio(ethylideneamino)-N-methyl-N-(morpholinothio)carbamate (UC 51717), triazamate;

3. from the group comprising carboxylates acrinathrin, allethrin, alphametrin, beta-cypermethrin, 5-benzyl-3-furylmethyl-(E)-, (1R)-cis-2,2-di-methyl-3-(2-oxothiolan-3-ylidenemethyl)cyclopropanecarboxylate, beta-cyfluthrin, bioallethrin, bioallethrin((S)-cyclopentylisomer), bioresmethrin, bifenthrin, (RS)-1-cyano-1-(6-phenoxy-2-pyridyl)methyl-(1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D-isomer), imiprothrin (SA41311), lambda-cyhalothrin, permethrin, phenothrin ((R)-isomer), prallethrin, pyrethrine (natural products), resmethrin, tefluthrin, tetramethrin, theta-cypermethrin (TD-2344), tralomethrin, transfluthrin, zeta-cypermethrin (F-56701);

4. from the group comprising the amidines amitraz, chlordimeform;

5. From the group comprising the tin compounds cyhexatin, fenbutatinoxide;

6. Others abamectin, ABG-9008, acetamiprid, *Anagrapha falcitera*, AKD-1022, AKD-3059, ANS-118, *Bacillus thuringiensis, Beauveria bassiana*, bensultap, bifenazate (D-2341), binapacryl, BJL-932, bromopropylate, BTG-504, BTG-505, buprofezin, camphechlor, cartap, chlorbenzilate, chlorfenapyr, chlorfluazuron, 2-(4-chlorophenyl)4,5-diphenylthiophene (UBI-T 930), chlorfentezine, chromafenozide (ANS-118), CG-216, CG-217, CG-234, A-184699, 2-naphthylmethyl cyclopropanecarboxylate (Ro12-0470), cyromazin, diacloden (thiamethoxam), diafenthiuron, ethyl N-(3,5-dichloro-4-(1,1,2,3,3,3-hexafluoro-1-propyloxy)phenyl)carbamoyl)-2-chlorobenzocarboximidate, DDT, dicofol, diflubenzuron, N-(2,3-dihydro-3-methyl-1,3-thiazol-2-ylidene)-2,4-xylidine, dinobuton, dinocap, diofenolan, DPX-062, emamectin-benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)4-methyl-1-pentyl)diphenyl ether (MTI 800), granulosis and nuclear polyhedrosis viruses, fenpyroximate, fenthiocarb, flubenzimine, flucycloxuron, flufenoxuron, flufenprox (ICI-A5683), fluproxyfen, gamma-HCH, halofenozide (RH-0345), halofenprox (MTI-732), hexaflumuron (DE_473), hexythiazox, HOI-9004, hydramethyinon (AC 217300), lufenuron, imidacloprid, indoxacarb (DPX-MP062), kanemite (AKD-2023), M-020, MTI-446, ivermectin, M-020, methoxyfenozide (intrepid, RH-2485), milbemectin, NC-196, Neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-1 96, NC-1111, NNI-9768, novaluron (MCW-275), OK-9701, OK-9601, OK-9602, propargite, pymethrozine, pyridaben, pyrimidifen (SU-8801), RH-0345, RH-2485, RYI-210, S-1283, S-1833, SB7242, Sl-8601, silafluofen, silomadine (CG-177), spinosad, SU-9118, tebufenozide, tebufenpyrad (MK-239), teflubenzuron, tetradifon, tetrasul, thiacloprid, thiocyclam, TI-435, tolfenpyrad (OMI-88), triazamate (RH-7988), triflumuron, verbutin, vertalec (mykotal), YI-5301.

The abovementioned components are known active substances, many of which are described in C.D.S. Tomlin, S.B. Walker, The Pesticide Manual, 11th Edition (1997), British Crop Protection Council.

The active substance content of the use forms prepared from the commercially available formulations can vary within broad ranges. The active compound concentration of the use forms can be from 0.0001 to 95% by weight of active substance, preferably between 0.0001 and 1 % by weight. Application is effected in a conventional fashion, matched to the use forms.

The active substance content of the use forms prepared from the commercially available formulations can be from 0.00000001 to 95% by weight of active substance, preferably between 0.00001 and 1 % by weight.

Application is effected in a conventional fashion matched to the use forms.

The active substances according to the invention are also suitable in the field of veterinary medicine, preferably for controlling endo- and ectoparasites, or in the field of animal husbandry.

The active substances according to the invention are preferably applied in a known fashion, such as by oral application in the form of, for example, tablets, capsules, potions or granules, by dermal application in the form of, for example, dipping, spraying, pouring-on and spotting-on and dusting, and also by parenteral application in the form of, for example, injection.

The novel compounds of the formula (I) according to the invention can accordingly also be employed particularly advantageously in livestock husbandry (for example cattle, sheep, pigs and poultry such as chickens and geese). In a preferred embodiment of the invention, the compounds of the formula (I), if appropriate in suitable formulations (cf. above) and if appropriate with the drinking water or feed, are administered orally to the animals. Since excretion in the faeces occurs in an effective fashion, the development of insects in the animal faeces can be prevented very simply in this fashion. The dosages and formulations suitable in each case, in particular, depend on the type and developmental stage of the productive animals and also on the severity of infestation and can easily be determined and fixed by conventional methods. In the case of cattle, the compounds can be employed, for example, in dosages of 0.01 to 1 mg/kg of body weight.

The compounds of the formula (I) according to the invention are also distinguished by an outstanding fungicidal action. Fungal pathogens which have already penetrated plant tissue can successfully be controlled in the curative way. This is particularly important and advantageous in the case of those fungal diseases which, once infection has taken place, can no longer be controlled efficiently with the fungicides normally available. The spectrum of action of the claimed compounds extends to a variety of economically important phytopathogenic fungi such as, for example, *Plasmopara viticola, Phytophthora infestans, Erysiphe graminis, Pyricularia oryzae, Pyrenophora teres, Leptosphaerea nodorum* and *Pellicularia sasakii* and *Puccinia recondite*.

In addition, the compounds according to the invention are also suitable for use in industrial fields, for example as wood preservative, as preservative in paints, in cooling lubricants for metal working or as preservative in drilling and cutting oils.

The active compounds according to the invention, in their commercially available formulations, can be used either alone or in combination with other fungicides known from the literature.

Examples of fungicides which are known from the literature and which can be combined in accordance with the invention with the compounds of the formula (I) are the following products:

aldimorph, andoprim, anilazine, BAS 480F, BAS 450F, benalaxyl, benodanil, benomyl, binapacryl, bitertanol, bromuconazole, buthiobate, captafol, captan, carbendazim, carboxin, CGA 173506, cyprofuram, dichlofluanid, dichlomezin, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazol, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanil, flutriafol, folpet, fosetyl-aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds such as copper oxychloride, oxine-copper, copper oxide, mancozeb, maneb, mepanipyrim (KIF 3535), metconazole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiofanate-methyl, thiram, tolclofos-methyl, tolylfluanid, triadimefon, triadimenol, tricyclazole, tridemorph, triflumizole, triforine, validamycin, vinchlozolin, XRD 563, zineb, sodium dodecylsulfonate, sodium dodecyl sulfate, sodium C13/C15-alcohol ether sulfonate, sodium cetostearyl phosphate ester, sodium dioctylsulfosuccinate, sodium isopropyinaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quarternized fatty amines, alkyldimethylbenzylammonium chloride and 1-hydroxylethyl-2-alkylimidazoline.

The abovementioned components are known active substances, many of which are described in C. D. S. Tomlin, S. B. Walker, The Pesticide Manual, 11th Edition (1997), British Crop Protection Council.

The active substance content of the use forms prepared from the commercially available formulations can vary within broad ranges. The active substance concentration of the use forms can be from 0.0001 to 95% by weight of active substance, preferably between 0.0001 and 1 % by weight. Application is effected in a conventional fashion, matched to the use forms.

The compounds of the formula (I) can also be employed for controlling harmful organisms in crops of known or genetically engineered plants yet to be developed. As a rule, the transgenic plants are distinguished by particular advantageous properties, for example by resistances to certain crop protection agents, resistances to plant diseases or pathogens of plant diseases such as certain insects or microorganisms such as fungi, bacteria or viruses. Other particular properties relate, for example, to the harvested material with regard to quantity, quality, storage properties, composition and specific constituents. Thus, transgenic plants with an elevated starch content or altered starch quality, or those with a different fatty acid spectrum of the harvested material are known.

The use in economically important transgenic crops of useful plants and ornamentals, for example, cereals such as wheat, barley, rye, oats, millet and sorghum, rice, cassava and maize or else crops of sugar beet, cotton, soya, oilseed rape, potatoes, tomatoes, peas and other vegetables is preferred.

When using in transgenic crops, in particular those with resistances to insects, effects are frequently found (in addition to the pesticidal effects which can be observed in other crops) which are specific to application in the transgenic crop in question, for example an altered or specifically widened spectrum of pests which can be controlled, or altered application rates which can be used for application.

The invention therefore also relates to the use of compounds of the formula (I) for controlling harmful organisms in transgenic crop plants.

The contents of german patent application 198 15 026.1, whose priority is claimed by the present application, and the contents of the appended summary are incorporated herein specifically by way of reference; they are considered as part of the present description by way of citation:

The examples which follow serve to illustrate the invention without restricting them thereto.

A. FORMULATION EXAMPLES

1a) A dust is obtained by mixing 10 parts by weight of active substance and 90 parts by weight of talc as inert substance and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water, and grinding the mixture in a ball mill to a fineness of below 5 microns.

d) An emulsifiable concentrate can be prepared from 15 parts by weight of active substance, 75 parts by weight of cyclohexane as solvent and 10 parts by weight of oxyethylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, dried and mixed intimately. The wettable powder amounts to approx. 5% by weight and the inert carrier material to approx. 95% of the finished granules.

B. PREPARATION EXAMPLES

Example A

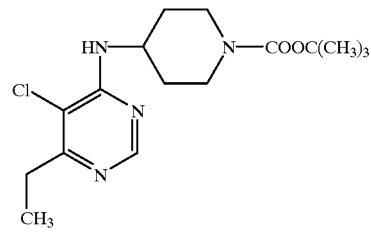

4-(N-tert-butoxycarbonylpiperidin-1-ylamino)-5-chloro-6-ethylpyrimidine 17.7 g (0.10 mol) of 4,5-dichloro-6-ethylpyrimidine, 20.0 g 1-(tert-butoxycarbonyl)4-aminopiperidine (0.10 mol) and 15.2 g (0.15 mol) of triethylamine were heated for 8 hours at 80–90°. After cooling, the mixture was worked up with water/dichloromethane and the organic phase was dried and concentrated. For purification, the crude product was chromatographed on silica gel (petroleum ether/ethyl acetate 1:1). This gave 21.7 g (63.6% of theory) of a colorless oil which solidified gradually.

M.p. 78–79° C.

Preparation of the starting matererial 1-(tert-butoxycarbonyl)4-aminopiperidine 100.0 g (0.50 mol) of 1-tert-butoxycarbonyl-4-piperidone were subjected to reductive amination in 300 ml of ammonia-saturated methanol in the presence of 20.0 g of Raney nickel at 100° C. and a hydrogen pressure of 100 bar. After the catalyst had been removed by filtration, the mixture was concentrated. This gave 95.5 g of a brown oil (95.4% of theory).

Example B

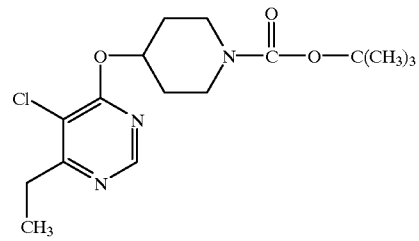

4-(1-tert-butoxycarbonylpiperidin-4-yloxy)-5-chloro-6-ethylpyrimidine 0.4 g (10 mmol) of sodium hydride (80% dispersion in oil) was added to a solution of 2.0 g (10 mmol) of 1-(tert-butoxycarbonylpiperidin-4-ol and 1.8 g (10 mmol) of 4,5-dichloro-6-ethylpyrimidine in 25 ml of tetrahydrofuran, and the mixture was stirred for 2 hours at room temperature for 1 hour at reflux. After cooling, the mixture was concentrated, the residue was taken up in water/toluene, and the organic phase was dried and concentrated. For purification, the product was chromatographed on silica gel (petroleum ether/ethyl acetate 7:3). This gave 2.5 g (73.5% of theory) of a yellow oil.

¹H NMR (CDCl₃): δ=8.51 (s, 1H, pyrimidinde-H); 5.38 (m, 1H, OC$\underline{H}$); 4.70 (m, 2H, piperidine-H); 3.42 (m, 2H, piperidine-H); 2.90 (q, 2H, $\underline{CH_2}$CH₃); 1.98 (m, 2H, piperidine-H); 1.8 (m, 2H, piperidine-H); 1.48 (s, 9H, tert-butyl); 1.39 (tr, 3H, CH₂$\underline{CH_3}$)

Example C

Intermediate

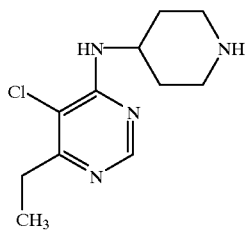

5-chloro-6-ethyl-4-(piperidin-4-ylamino)pyrimidine 20.7 g (0.61 mmol) of 4-(tert-butoxycarbonylpiperidin-4-ylamino)-5-chloro-6-ethylpyrimidine (Example A) were dissolved in 100 ml of dichloroethane and 148.0 g of trifluorocetic acid were added slowly. After the evolution of CO₂ had ceased, stirring was continued for 2 more hours. After the solvent and the trifluoroacetic acid had been stripped off, the mixture was concentrated and the residue was taken up in dichloromethane/water. After the mixture had been rendered weakly alkaline by addition of dilute sodium hydroxide solution, the organic phase was separated off, dried and concentrated. This gave 12.3 g (83.9% of theory) of a yellow solid.

M.p.: 150–151° C.

Example D

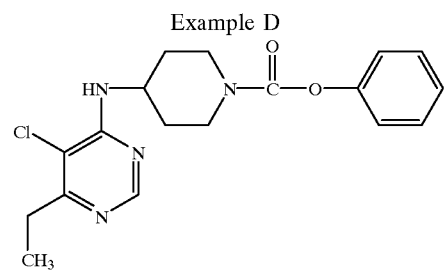

5-chloro-6-ethyl-4-(1-phenoxycarbonylpiperidin-4-ylamino)pyrimidine 1.2 g (5 mmol) of 5-chloro-6-ethyl-4-(pipderidin-4-ylamino)pyrimidine (Example C) and 0.6 g (6 mmol) of triethylamine were introduced into 20 ml of dichloromethane, and 0.9 g (6 mmol) of phenyl chloroformate was added dropwise at 20–30° C. After the mixture had been left to stand overnight, it was extracted by stirring with water, and the organic phase was dried and concentrated. For purification, the product was chromatographed on silica gel (petroleum ether/ethyl acetate 1:1). This gave 1.4 g (77.6% of theory) of product as colorless solid.

M.p.: 105–106° C.

Other examples which can be prepared analogously to the synthetic examples mentioned above are those of Table 1 given hereinbelow.

TABLE 1

| Ex. No. | R₁ | R₂ | R₃ | A | Y | Z | X | R₅ | Physical Data |
|---|---|---|---|---|---|---|---|---|---|
| 1 | H | C₂H₅ | Cl | N | O | O | NH | methyl | |
| 2 | H | C₂H₅ | Cl | N | O | S | NH | methyl | m.p. 91–92° C. |
| 3 | H | C₂H₅ | Cl | N | S | S | NH | methyl | |
| 4 | H | C₂H₅ | Cl | N | O | O | NH | ethyl | |
| 5 | H | C₂H₅ | Cl | N | O | O | NH | n-propyl | |
| 6 | H | C₂H₅ | Cl | N | O | O | NH | i-propyl | m.p. 65–66° C. |
| 7 | H | C₂H₅ | Cl | N | O | O | NH | n-butyl | |
| 8 | H | C₂H₅ | Cl | N | O | O | NH | i-butyl | oil |
| 9 | H | C₂H₅ | Cl | N | O | O | NH | sec-butyl | |
| 10 | H | C₂H₅ | Cl | N | O | O | NH | tert-butyl | m.p. 78–79° C. |
| 11 | H | C₂H₅ | Cl | CH | O | O | NH | tert-butyl | |
| 12 | H | C₂H₅ | Cl | N | O | S | NH | tert-butyl | |
| 13 | H | C₂H₅ | Cl | N | S | S | NH | tert-butyl | |
| 14 | CH₃ | C₂H₅ | Cl | N | O | O | NH | tert-butyl | |
| 15 | Cl | C₂H₅ | Cl | N | O | O | NH | tert-butyl | |
| 16 | F | C₂H₅ | Cl | N | O | O | NH | tert-butyl | |
| 17 | H | CH₂OCH₃ | OCH₃ | N | O | O | NH | tert-butyl | oil |
| 18 | H | CH₂OCH₃ | OCH₃ | N | O | S | NH | tert-butyl | |
| 19 | H | CH₂OCH₃ | OCH₃ | N | S | S | NH | tert-butyl | |
| 20 | H | C₂H₅ | CH=CH₂ | N | O | O | NH | tert-butyl | |
| 21 | H | C₂H₅ | C≡CH | N | O | O | NH | tert-butyl | |
| 22 | H | CHFCH₃ | Cl | N | O | O | NH | tert-butyl | |
| 23 | H | C₂H₅ | Cl | N | O | O | O | tert-butyl | oil |
| 24 | H | CH₂OCH₃ | OCH₃ | N | O | O | O | tert-butyl | |
| 25 | H | C₂H₅ | Cl | N | O | O | NH | n-pentyl | |
| 26 | H | C₂H₅ | Cl | N | O | O | NH | C(CH₃)₂C₂H₅ | |
| 27 | H | C₂H₅ | Cl | N | O | O | NH | CH₂C(CH₃)₃ | m.p. 104–105° C. |
| 28 | H | C₂H₅ | Cl | N | O | O | NH | n-hexyl | |

TABLE 1-continued

| Ex. No. | R$_1$ | R$_2$ | R$_3$ | A | Y | Z | X | R$_5$ | Physical Data |
|---|---|---|---|---|---|---|---|---|---|
| 29 | H | C$_2$H$_5$ | Cl | N | O | O | NH | n-heptyl | |
| 30 | H | C$_2$H$_5$ | Cl | N | O | O | NH | n-octyl | oil |
| 31 | H | C$_2$H$_5$ | Cl | N | O | O | NH | CH$_2$CF$_3$ | |
| 32 | H | C$_2$H$_5$ | Cl | N | O | O | NH | CH$_2$CCl$_3$ | oil |
| 33 | H | C$_2$H$_5$ | Cl | N | O | O | NH | CH$_2$CH$_2$OCH$_3$ | |
| 34 | H | C$_2$H$_5$ | Cl | N | O | O | NH | CH$_2$CH=CH$_2$ | |
| 35 | H | C$_2$H$_5$ | Cl | N | O | O | NH | CH$_2$—CH=CH—CH$_3$ | |
| 36 | H | C$_2$H$_5$ | Cl | N | O | O | NH | CH$_2$—C≡CH | |
| 37 | H | C$_2$H$_5$ | Cl | N | O | O | NH | CH$_2$—C≡C—CH$_3$ | |
| 38 | H | C$_2$H$_5$ | Cl | N | O | O | NH | benzyl | m.p. 120–121° C. |
| 39 | H | C$_2$H$_5$ | Cl | N | O | O | NH | 4-fluorobenzyl | |
| 40 | H | C$_2$H$_5$ | Cl | N | O | O | NH | 4-chlorobenzyl | |
| 41 | H | C$_2$H$_5$ | Cl | N | O | O | NH | 4-methylbenzyl | |
| 42 | H | C$_2$H$_5$ | Cl | N | O | O | NH | 4-trifluoromethyl-benzyl | |
| 43 | H | C$_2$H$_5$ | Cl | N | O | O | NH | 4-methoxybenzyl | |
| 44 | H | C$_2$H$_5$ | Cl | N | O | O | NH | 1-phenylethyl | |
| 45 | H | C$_2$H$_5$ | Cl | N | O | O | NH | 2-phenylethyl | |
| 46 | H | C$_2$H$_5$ | Cl | N | O | O | NH | C(CH$_3$)$_2$CCl$_3$ | m.p. 125–126° C. |
| 47 | H | C$_2$H$_5$ | Cl | N | O | O | NH | cinnamyl | |
| 48 | H | C$_2$H$_5$ | Cl | N | O | O | NH | phenylpropargyl | |
| 49 | H | C$_2$H$_5$ | Cl | N | O | O | NH | phenyl | m.p. 105–106° C. |
| 50 | H | C$_2$H$_5$ | Cl | N | O | O | O | phenyl | |
| 51 | H | C$_2$H$_5$ | Cl | CH | O | O | NH | phenyl | |
| 52 | H | C$_2$H$_5$ | Cl | N | S | O | NH | phenyl | m.p. 117–119° C. |
| 53 | H | C$_2$H$_5$ | Cl | N | S | S | NH | phenyl | m.p. 123–124° C. |
| 54 | H | C$_2$H$_5$ | Cl | N | O | S | NH | phenyl | |
| 55 | CH$_3$ | C$_2$H$_5$ | Cl | N | O | O | NH | phenyl | |
| 56 | Cl | C$_2$H$_5$ | Cl | N | O | O | NH | phenyl | |
| 57 | F | C$_2$H$_5$ | Cl | N | O | O | NH | phenyl | |
| 58 | H | CH$_2$OCH$_3$ | OCH$_3$ | N | O | O | NH | phenyl | |
| 59 | H | C$_2$H$_5$ | CH=CH$_2$ | N | O | O | NH | phenyl | |
| 60 | H | C$_2$H$_5$ | C≡CH | N | O | O | NH | phenyl | |
| 61 | H | CHFCH$_3$ | Cl | N | O | O | NH | phenyl | |
| 62 | H | C$_2$H$_5$ | Cl | N | O | O | NH | 4-fluorophenyl | m.p. 118–119° C. |
| 63 | H | C$_2$H$_5$ | Cl | N | O | O | NH | 4-chlorophenyl | |
| 64 | H | C$_2$H$_5$ | Cl | N | O | O | NH | 4-methylphenyl | m.p. 127–128° C. |
| 65 | H | C$_2$H$_5$ | Cl | N | O | O | NH | 4-methoxyphenyl | m.p. 123–124° C. |
| 66 | H | C$_2$H$_5$ | Cl | N | O | O | NH | 4-trifluoromethyl-phenyl | |
| 67 | H | C$_2$H$_5$ | Cl | N | O | O | NH | 4-carbomethoxy-phenyl | m.p. 152–153° C. |
| 68 | H | C$_2$H$_5$ | Cl | N | O | O | NH | 2,4-difluorophenyl | m.p. 115–116° C. |
| 69 | H | C$_2$H$_5$ | Cl | N | O | O | NH | 2-fluoro-4-chloro-phenyl | m.p. 123–124° C. |
| 70 | H | C$_2$H$_5$ | Cl | N | O | O | NH | 2-chloro-4-fluoro-phenyl | m.p. 126–127° C. |
| 71 | H | C$_2$H$_5$ | Cl | N | O | O | NH | 2,6-difluorophenyl | |
| 72 | H | C$_2$H$_5$ | Cl | N | O | O | NH | 2,6-dichloro-phenyl | |
| 73 | H | C$_2$H$_5$ | Cl | N | O | O | NH | 2,4,6-trichloro-phenyl | |
| 74 | H | C$_2$H$_5$ | Cl | N | S | O | NH | 2,4,6-trichloro-phenyl | oil |
| 75 | H | C$_2$H$_5$ | Cl | N | S | O | NH | 4-methylphenyl | m.p. 158–160° C. |
| 76 | H | C$_2$H$_5$ | Cl | N | S | O | NH | 4-fluorophenyl | m.p. 158–159° C. |
| 77 | H | C$_2$H$_5$ | Cl | N | S | O | NH | 4-chlorophenyl | m.p. 110–112° C. |
| 78 | H | C$_2$H$_5$ | Cl | N | O | O | NH | 2-thienyl | |
| 79 | H | C$_2$H$_5$ | Cl | N | O | O | NH | 3-thienyl | |
| 80 | H | C$_2$H$_5$ | Cl | N | O | O | NH | 2-pyridyl | |
| 81 | H | C$_2$H$_5$ | Cl | N | O | O | NH | 3-pyridyl | |
| 82 | H | C$_2$H$_5$ | Cl | N | O | O | NH | 4-pyridyl | |
| 83 | H | C$_2$H$_5$ | Cl | N | O | O | NH | cyclopropyl | |
| 84 | H | C$_2$H$_5$ | Cl | N | O | O | NH | cyclobutyl | |
| 85 | H | C$_2$H$_5$ | Cl | N | O | O | NH | cyclopentyl | |
| 86 | H | C$_2$H$_5$ | Cl | N | O | O | NH | cyclohexyl | |

TABLE 1-continued

| Ex. No. | R₁ | R₂ | R₃ | A | Y | Z | X | R₅ | Physical Data |
|---|---|---|---|---|---|---|---|---|---|
| 87 | H | C₂H₅ | Cl | N | O | O | NH | 1-methylcyclopentyl | |
| 88 | H | C₂H₅ | Cl | N | O | O | NH | 1-methylcyclohexyl | |
| 89 | H | C₂H₅ | Cl | N | O | O | NH | tetrahydrofurfuryl | |
| 90 | H | C₂H₅ | Cl | N | O | O | NH | 1,2,3,4-tetrahydro-1-naphthyl | |
| 91 | H | C₂H₅ | Cl | N | O | O | NH | 1,2,3,4-tetrahydro-2-naphthyl | |
| 92 | H | C₂H₅ | Cl | N | O | O | NH | 5,6,7,8-tetrahydro-1-naphthyl | |
| 93 | H | C₂H₅ | Cl | N | O | O | NH | 5,6,7,8-tetrahydro-2-naphthyl | |
| 94 | H | C₂H₅ | Cl | N | S | NH | NH | phenyl | |
| 95 | H | C₂H₅ | Cl | N | O | NH | NH | p-tolyl | m.p. 173–174° C. |
| 96 | H | C₂H₅ | Cl | N | O | NH | NH | p-fluorophenyl | m.p. 191–192° C. |
| 97 | H | C₂H₅ | Cl | N | O | NH | NH | p-isopropylphenyl | m.p. 131–132° C. |
| 98 | H | C₂H₅ | Cl | N | O | NH | NH | tert-butyl | m.p. 138–139° C. |
| 99 | H | C₂H₅ | Cl | N | O | NH | NH | cyclohexyl | m.p. 160–162° C. |
| 100 | H | C₂H₅ | Cl | N | O | NCH₃ | NH | phenyl | m.p. 92–94° C. |
| 101 | H | C₂H₅ | Cl | N | S | NCH₃ | NH | methyl | m.p. 135–136° C. |
| 102 | H | C₂H₅ | Cl | N | NO₂ | NH | NH | H | m.p.210–212° C. decomposition |
| 103 | H | C₂H₅ | Cl | N | NCN | S | NH | CH₃ | m.p. 163–164° C. |
| 104 | H | C₂H₅ | Cl | N | NCN | NH | NH | n-octyl | m.p. 93–94° C. |
| 105 | H | C₂H₅ | Cl | N | NCN | NH | NH | 2-octyl | m.p. 142–143° C. |

OTHER EXAMPLES

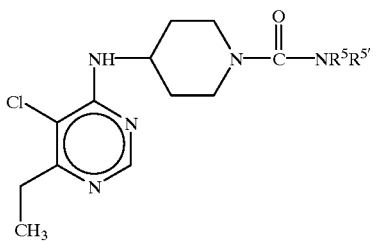

Example 106

NR⁵R⁵'=pyrrolidine m.p. 93–94° C.

Example 107

NR⁵R⁵'=morpholine m.p. 146–147° C.

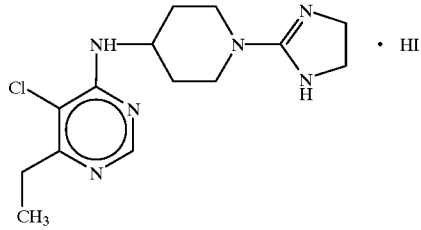

Example 108 m.p. 225–226° C.

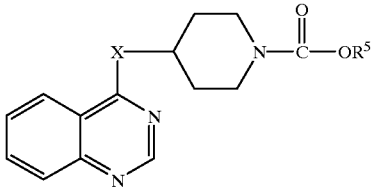

Example 110

X=NH  R⁵=tert-butyl

Example 111

X=NH  R⁵=phenyl

Example 112

X=O  R⁵=tert-butyl

Example 113

X=O R⁵=phenyl

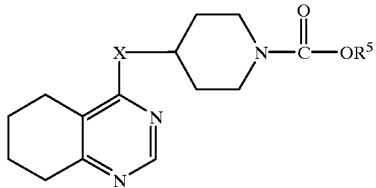

Example 114

X=NH R⁵=tert-butyl

Example 115

X=NH R⁵=phenyl

Example 116

X=O R⁵=tert-phenyl

Example 117

X=O R⁵=phenyl

BIOLOGICAL EXAMPLES

Use as Fungicide

The compounds were tested for their activity against one or more of the following organisms:

*Plasmopara viticola*
*Erysphe graminis* f. sp. *tritici*
*Pyricularia oryzae*
*Leptosphaeria nodorum*

Aqueous solutions of dispersions of the compounds of the desired concentration with addition of a wetter were applied to leaves or stems of the test plant. The plants, or parts of the plants, were inoculated with the test pathogen in question and kept under controlled environmental conditions which are suitable for plant growth and disease development. After a suitable time, the extent of infection of the diseased plant was estimated visually. The compounds are assessed using a scale from 1 to 3 in which 1 means none to poor control, 2 moderate control and 3 good to complete control. At a concentration of 500 ppm or less, the following compounds scored 2 or more against the fungi mentioned.

Example A

Action against *Erysiphe graminis* f. sp. *tritici* (Powdery Mildew of Wheat)

The following compounds scored 2 or more: Example No.: 10.

Example B

Action against *Plasmopara viticola* (Downy Mildew)

The following compounds scored 2 or more: Examples No.: 6, 7, 8, 10, 27, 46, 49, 62, 68.

Example C

Action against *Phytophthora infestans*

The following compounds scored 2 or more. Examples No.: 6, 8, 10, 23, 49, 64, 68.

Example D

Action against *Leptosphaeria nodorum*

The following compounds scored 2 or more. Examples No.: 10, 62, 68.

Example E

Action against *Pyricularia oryzae*

The following compounds scored 2 or more. Examples No.: 7, 62.

Use as Acaricide, Insecticide, Nematicide

Example F

Action against *Tetranychus urticae* (Immersion Test)

Sliced bean plant (*Phaseolus vulgaris*) stalks bearing one leaf were transferred into amber glass bottles filled with tap water and then populated with approx. 100 spider mites (*Tetranychus urticae*). Leaf and spider mites were then immersed for 5 seconds in an aqueous solution of the formulated preparation to be tested. Plant and animals were left to drain and then stored in a controlled-environment cabinet (16 hours light/day, 25° C., 40–60% relative humidity). The efficacy of the preparation on all stages of the spider mites was determined after storing for 6 days. At a concentration of 300 ppm (based on active substance content), a 90–100% mortality was caused by the preparations of Examples No. 2, 6, 7, 8,10, 17, 23, 27, 46, 52, 53, 49, 62, 65, 68, 69, 70, 75 and 77.

Example G

Action against *Aphis fabae*

Germinated seeds of field beans (*Vicia faba*) with germinal roots were transferred into amber glass bottles filled with tap water and subsequently populated with approx. 100 black bean aphids (*Aphis fabae*). Plants and aphids were then immersed for 5 seconds in an aqueous solution of the formulated preparation to be tested. Plant and animals were left to drain and then stored in a controlled-environment cabinet (16 hours light/day, 25° C., 40–60% relative humidity). The efficacy of the preparation on the aphids was determined after storing for 3 and 6 days. At a concentration of 300 ppm (based on active substance content), a 90–100% aphid mortality was caused by the preparations of Examples No. 6, 7, 8, 10, 17, 23, 49, 53, 62, 64, 65, 68, 70, 75 and 76.

Example H

Action against *Nilaparvata lugens*

The leaves of 12 rice plants of tiller length 8 cm were immersed for 5 seconds in an aqueous solution of the formulated preparation to be tested. After the treated rice plants had been left to drain, they were placed into a Petri dish and populated with approx. 20 (L3 instar) larvae of the rice leaf hopper species *Nilaparvata lugens*. The Petri dish was covered and stored in a controlled-environment cabinet (16 hours light/day, 25° C., 40–60% relative humidity). The mortality of the leaf hopper larvae was determined after storage for 6 days. At a concentration of 300 ppm (based on active substance content), a 90–100% mortality was caused by the preparations of Examples No. 6, 7, 8, 49, 52, 53, 62, 64, 65, 68, 70, 75 and 96.

Example I

Action against *Heliothis virescens* (Ovicidal Action)

A Petri dish whose bottom had been covered with filter paper and contained approx. 5 ml of nutrient medium was prepared. Filter paper sections containing approximately 30 24-hour-old tobacco budworm (Heliothis virescens) eggs were immersed for 5 seconds into an aqueous solution of the formulated preparation to be tested and subsequently placed in the Petri dish. A further 200 pi of the aqueous solution were distributed over the nutrient medium. The Petri dish was covered and stored in a controlled-environment cabinet at approx. 25° C. The efficacy of the 1 preparation on the eggs and any larvae which may have hatched was determined after storage for 6 days. At a concentration of 300 ppm (based on active substance content), a 90–100% mortality was caused by the preparations of Examples No. 2, 6, 7, 8, 10,17, 23, 49, 52, 53, 62, 64, 65, 68, 69, 70, 75, 76 and 100.

Example J

Action against *Spodoptera litoralis*

A Petri dish whose bottom had been covered with filter paper and contained approx. 5 ml of nutrient medium was prepared. Five L2 larvae of the Egyptian cotton leafworm (*Spodoptera litoralis*) were counted into a small beaker. 200 μl of an aqueous solution of the formulated preparation to be tested were pipetted into the beaker. The treated larvae were then poured into the Petri dish, and a further 200 pi of the aqueous solution were distributed over the nutrient medium. After the Petri dish had been covered, it was stored in a controlled-environment cabinet at approx. 25° C. The action of the preparation on the larvae was determined after storage for 6 days. At a concentration of 300 ppm (based on active substance content), a larval mortality of 90–100% was caused by the preparations of Examples No. 6, 7, 8, 49, 53, 62, 64, 65, 68 and 70.

Example K

Action against *Meloidogyne incognita* (Nematicidal Action)

In a glass vessel, an aqueous solution of the formulated preparation to be tested (final volume 20 ml) was added to approx. 3000 newly hatched active (mobile) root gall nematode larvae (Meloidogyne incognita) (2nd instar). After the nematode larvae had been exposed continuously to the preparation for 6 days, the percentage of the individuals rendered immobile by the effect of the preparation was determined in comparison with untreated controls (percent nematicidal contact action). At a concentration of 3 ppm, based on active substance content, a 90–100% action against the root gall nematode *Meloidogyne incognita* was caused by the preparations of Examples No. 53, 65 and 69.

Example L

Action against *Diabrotica undecimpunctata*

A Petri dish whose bottom was half covered with filter paper and contained a germinated maize kernel on a damp cotton wool pad was prepared. Approx. 50 4–5-day-old corn budworm (Diabrotica undecimpunctata) eggs were transferred to the filter paper. Three drops of 200 μl of an aqueous solution of the formulated preparation to be tested were pipetted onto the eggs and the remainder onto the 7 maize kernel. The Petri dish was covered and then stored in a controlled-environment cabinet at approx. 25° C. The efficacy of the preparation on the eggs and any larvae which may have hatched was determined after storage for 6 days. At a concentration of 300 ppm (based on active substance content), a 90–100% mortality was caused by the preparations of Examples No. 6, 7, 8, 23, 46, 49, 53, 62, 68 and 70.

Example M

Action against *Carpocapsa pomonella* (Ovicidal Action)

Approximately 20 codling moth (*Carpocapsa pomonella*) eggs were introduced into a Petri dish filled with nutrient medium. Nutrient medium and eggs were then sprayed with an aqueous solution of the formulated preparation to be tested. The Petri dish was then covered with a lid. After storage at approx. 23° C. for 8 days, the action of the preparation on the eggs and any larvae hatched from them was determined. At a concentration of 300 ppm (based on active substance content), a 90–100% mortality was caused by the preparations of Examples No. 10 and 62.

Use as Antiparasitic

Example N

In vitro test on tropical cattle ticks (*Boophilus microplus*)

The efficacy of the compounds according to the invention against ticks were determined in the following experimental set-up:

To prepare a suitable preparation of active substance, a 10% (w/v) solution was prepared in a mixture consisting of dimethylformamide (85 g), nonylphenol polyglycol ether (3 g) and oxethylated castor oil (7 g), and the resulting emulsion concentrates were diluted with water to a test concentration of 1000 ppm. Batches of ten females of the tropical tick *Boophilus microplus* which had sucked themselves full were immersed for five minutes in this dilution of the active substance. The ticks were subsequently dried on filter paper and then placed with their backs on an adhesive film for oviposition purposes. The ticks were kept in an incubator at 28° C. and an atmospheric humidity of 90%.

As a control, female ticks were immersed in just water. The efficacy was assessed on the basis of the inhibition of oviposition two weeks after the treatment. In this test, a 100% inhibition of oviposition was caused by each of the compounds of Examples No. 6, 10, 17, 27, 46, 49, 53, 62, 64 and 69.

What is claimed is:

1. A compound of the formula (I)

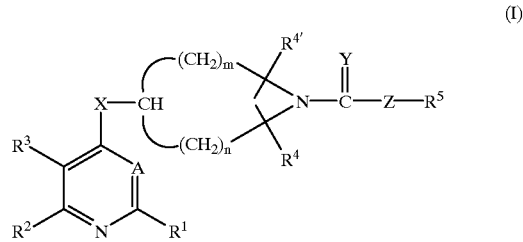

(I)

in which

R$^1$ is hydrogen, halogen, (C$_1$–C$_8$)-alkyl, (C$_1$–C$_8$)-haloalkyl, (C$_1$–C$_8$)-alkoxy or (C$_3$–C$_6$)-cycloalkyl;

R$^2$ and R$^3$ are identical or different and in each case are hydrogen, (C$_1$–C$_8$)-alkyl, (C$_2$–C$_8$)-alkenyl, (C$_2$–C$_8$)-alkynyl, (C$_1$–C$_8$)-alkoxy, halogen, hydroxyl, cyano, nitro, thiocyano, (C$_1$–C$_8$)-alkanoyl, (C$_1$–C$_8$)-alkoxycarbonyl, (C$_1$–C$_8$)-alkylthio, (C$_1$–C$_8$)-alkysulfinyl, (C$_1$–C$_8$)-alkylsulfonyl, amino, (C$_1$–C$_8$)-alkylamino, (C$_1$–C$_8$)-dialkylamino or (C$_3$–C$_6$)-cycloalkyl, it being possible for a saturated carbon unit in the alkyl, cycloalkyl, alkenyl and alkynyl radicals or the groups derived from these to be replaced by a hetero atom unit or dimethylsilyl, and it furthermore being possible for up to three hydrogen atoms in these radicals or in the groups derived from these to be replaced by halogen, in the case of fluorine it also being possible for all hydrogen atoms to be replaced by fluorine; or R$^2$ and R$^3$ together with the carbon atoms to which they are bonded form an unsaturated 5- or 6-membered isocyclic ring which, if it is a 5-membered ring, optionally contains an oxygen or sulfur atom in place of CH$_2$ or which, if it is a 6membered ring, optionally contains one or two nitrogen atoms in place of one or two CH units and which is optionally substituted by 1, 2 or 3 identical or different radicals and these radicals are (($C_1$–$C_4$)-alkyl, ($C_1$–$C_4$)-haloalkyl, halogen, ($C_1$–$C_4$)-alkoxy or ($C_1$–$C_4$)-haloalkoyl; or $R^2$ and $R^3$ together with the carbon atoms to which they are bonded form a saturated 5-, 6- or 7-membered isocyclic ring which optionally contains oxygen and/or sulfur in place of one or two $CH_2$ groups and which is optionally substituted by 1, 2 or 3 ($C_1$–$C_4$)-alkyl groups;

A is N;

X is NH, oxygen or $S(O)_q$ where q=0, 1 or 2;

Y is oxygen, sulfur or a group $NR^{5'}$ or $NR^{5''}$ where $R^{5'}$ and $R^{5''}$ are identical or different and in each case have the meanings given hereinbelow for $R^5$, or, in the event that Y is a group $NR^{5'}$, $R^{5''}$ is additionally nitro, cyano, hydroxyl, alkoxy or a group $NR^{5'''}R^{5''''}$ where $R^{5'''}$ and $R^{5''''}$ are identical or different and in each case may have the meanings given hereinbelow for $R^5$, Z is oxygen m and n are both the number 2;

$R^4$ and $R^{4'}$ are hydrogen;

$R^5$ is alkyl, alkenyl, alkynyl, aryl, heterocyclyl, it being possible for the aryl or heterocyclyl radicals mentioned to be unsubstituted or to have attached to them up to three, in the case of fluorine also up to the maximum number of, identical or different radicals, and it being possible, in the alkyl, alkenyl or alkynyl radicals mentioned, for one or more non-adjacent saturated carbon units to be replaced by a carbonyl group or by hetero atom units;

and in which, in addition, 3 to 12 atoms of these hydrocarbon radicals which are optionally modified as above optionally form a cycle;

and it being possible for these hydrocarbon radicals, with or without the abovementioned variations, optionally to be substituted by one or more in the case of fluorine up to the maximum number of, identical or different radicals selected from the group consisting of halogen, aryl, aryloxy, arylthio, cycloalkyl, cycloalkoxy, cycloalkylthio, heterocyclyl, heterocyclyloxy, heterocyclthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyoxycarbonyl, alkanoyloxy, halogenalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of identical or different substituents, and it furthermore being possible, in the event that Y is a group $NR^{5'}$, $R^{5'}$ of group Y and $R^5$ of group Z to be linked to form a 5–8-membered heteroaliphatic ring system;

or a tautomer or salt thereof.

2. A compound of the formula (I) as claimed in claim 1 in which $R^1$ is hydrogen, halogen, ($C_1$–$C_4$)-alkyl, ($C_1$–$C_4$)-haloalkyl or ($C_3$–$C_5$)-cycloalkyl;

$R^2$ and $R^3$ are identical or different in each case are hydrogen; ($C_1$–$C_4$)-alkyl, ($C_1$–$C_4$)-haloalkyl, ($C_2$–$C_4$)-alkenyl, ($C_2$–$C_4$)-haloalkenyl, ($C_2$–$C_4$)-alkynyl, ($C_2$–$C_4$)-haloalkynyl, trimethylsilylalkynyl, ($C_1$–$C_4$)-alkoxy, ($C_1$–$C_4$)-haloalkoxy, ($C_1$–$C_4$)-alkoxy-($C_1$–$C_4$)-alkyl, ($C_1$–$C_4$)-haloalkoxy-($C_1$–$C_4$)-alkyl, ($C_1$–$C_4$)-alkoxy-($C_1$–$C_4$)-haloalkyl, ($C_1$–$C_4$)-haloalkoxy-($C_1$–$C_4$)-haloalkyl, halogen, hydroxyl, ($C_1$–$C_4$)-hydroxyalkyl, ($C_1$–$C_4$)-alkanoyl, ($C_1$–$C_4$)-haloalkanoyl, ($C_3$–$C_5$)-cycloalkyl, ($C_3$–$C_5$)-halocycloalkyl, cyano, ($C_1$–$C_4$)-cyanoalkyl, nitro, ($C_1$–$C_4$)-nitroalkyl, thiocyano, ($C_1$–$C_4$)-thiocyanoalkyl, ($C_1$–$C_4$)-alkoxycarbonyl, ($C_1$–$C_4$)-alkoxycarbonyl-($C_1$–$C_4$)-alkyl, ($C_1$–$C_4$)-haloalkoxycarbonyl, ($C_1$–$C_4$)-alkylthio, ($C_1$–$C_4$)-alkylthio-($C_1$–$C_4$)-alkyl, ($C_1$–$C_4$)-haloalkylthio, ($C_1$–$C_4$)-alkylsulfinyl, ($C_1$–$C_4$)-haloalkylsulfinyl, ($C_1$–$C_4$)-alkylsulfonyl, ($C_1$–$C_4$)-haloalkylsulfonyl, amino, ($C_1$–$C_4$)-alkylamino or ($C_1$–$C_4$)-dialkylamino; or $R^2$ and $R^3$ together with the carbon atoms to which they are bonded form an unsaturated 5- or 6-membered isocyclic ring which, if it is a 5-membered ring, optionally contains an oxygen or sulfur atom in place of $CH_2$ or which, if it is a 6-membered ring, optionally contains one or two nitrogen atoms in place of one or two CH units and which is optionally substituted by 1, 2 or 3 identical or different radicals, these radicals preferably being ($C_1$–$C_4$)-alkyl, ($C_1$–$C_4$)-haloalkyl, halogen, ($C_1$–$C_4$)-alkoxy or ($C_1$–$C_4$)-haloalkoxy; or $R^2$ and $R^3$ together with the carbon atoms to which they are bonded form a saturated 5-, 6- or 7-membered isocyclic ring which optionally contains oxygen and/or sulfur in place of one or two $CH_2$ groups and which is optionally substituted by 1, 2 or 3 ($C_1$–$C_4$)-alkyl groups, and $R^5$ is ($C_1$–$C_{20}$)-alkyl, ($C_2$–$C_{20}$)-alkenyl, ($C_2$–$C_{20}$)-alkynyl, aryl or heterocyclyl, it being possible for the aryl or heterocyclyl radicals mentioned to be unsubstituted or to have attached to them up to three, in the case of fluorine also up to the maximum number of, identical or different radicals and it being possible, in the alkyl, alkenyl or alkynyl radicals mentioned, for one or more nonadjacent saturated carbon units to be replaced by a carbonyl group or by hetero atom selected the group consisting of oxygen, $S(O)_x$ where x=0, 1 or 2, $NR^6$ or $SiR^7R^8$, $R^6$ being hydrogen, ($C_1$–$C_4$)-alkyl, ($C_1$–$C_4$)-alkoxy or ($C_1$–$C_4$)-alkanoyl and $R^7$ and $R^8$ are ($C_1$–$C_4$)-alkyl, and in which, moreover, 3 to 12 atoms of these hydrocarbon radicals which are optionally modified as above optionally form a cycle and it being possible for these hydrocarbon radicals, with or without the variations mentioned, to be optionally substituted by one or more, in the case of halogen up to the maximum number of, identical or different radicals selected from the group consisting of halogen, aryl, aryloxy, arylthio, ($C_3$–$C_8$)-cycloalkoxy, ($C_3$–$C_8$)-cycloalkylthio, heterocyclyl, heterocyclyloxy, heterocyclthio, ($C_1$–$C_{12}$)-alkanoyl, ($C_3$–$C_8$)-cycloalkanoyl, ($C_2$–$C_{12}$)-haloalkanoyl, aroyl, aryl-($C_1$–$C_4$)-alkanoyl, ($C_3$–$C_8$)-cycloalkyl-($C_1$–$C_4$)-alkanoyl, heterocyclyl-($C_1$–$C_4$)-alkanoyl, ($C_1$–$C_{12}$)-alkoxycarbonyl, ($C_1$–$C_{12}$)-haloalkoxycarbonyl, ($C_3$–$C_8$)-cycloalkoxycarbonyl, ($C_3$–$C_8$)-cycloalkyl-($C_1$–$C_4$)-alkoxycarbonyl, aryl-($C_1$–$C_4$)-alkoxycarbonyl, heterocyclyl-($C_1$–$C_4$)-alkoxycarbonyl, aryloxcarbonyl, heterocyclyloxycarbonyl, $(C_1-C_2)$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents; or a tautomer or salt thereof.

3. A compound of the formula (I) as claimed in claim 1 in which $R^1$ is hydrogen, fluorine, chlorine or methyl;

$R^2$ is $(C_1-C_4)$-alkyl, $(C_1-C_4)$-alkenyl, $(C_1-C_4)$-alkynyl, $(C_1-C_4)$-haloalkyl, methoxymethyl or cyano;

$R^3$ is hydrogen, halogen, methyl, ethyl, vinyl, halovinyl, $(C_1-C_2)$-fluoroalkyl, methoxy, ethoxy or cyano; or $R^2$ and $R^3$ together with the carbon atoms to which they are bonded form an optionally substituted unsaturated 5- or 6-membered ring, optionally contains a sulfur atom in place of a $CH_2$ unit; or $R^2$ and $R^3$ together with the carbon atoms to which they are bonded form a saturated 5- or 6-membered ring which optionally contains a sulfur or an oxygen atom in place of a $CH_2$ unit;

A is N;

X is NH or oxygen; and $R^4$ and $R^{4'}$ are hydrogen;

or a tautomer or salt thereof.

4. A compound of the formula (I) as claimed in claim 1 in which $R^1$ is hydrogen;

$R^2$ methyl, ethyl, propyl, isopropyl, $(C_1-C_2)$-fluoroalkyl, cyclopropyl or methoxymethyl;

$R^3$ is halogen, methyl, ethyl, ethynyl, vinyl, fluorovinyl, methoxy, ethoxy or cyano; or $R^2$ and $R^3$ together with the ring system to which they are bonded form the quinazoline or quinoline system which is optionally substituted by fluorine in the carbocyclic moiety; or $R^2$ and $R^3$ together with the carbon atoms to which they are bonded form a saturated 6-membered ring which optionally contains an oxygen or sulfur atom in place of a $CH_2$ group; and $R^4$ and $R^{4'}$ are hydrogen;

or a tautomer or salt thereof.

5. A compound of the formula (I) as claimed in 1 in which $R^1$ is hydrogen;

$R^2$ is methyl, ethyl, propyl, isopropyl, 1-fluoroethyl or methoxymethyl;

$R^3$ is fluorine, chlorine, bromine, cyano, vinyl, ethynyl or methoxy; or $R^2$ and $R^3$ together with the ring system to which they are bonded form the quinazoline system which is optionally substituted by a fluorine atom;

A is N;

X is NH;

$R^4$ and $R^{4'}$ are hydrogen;

or tautomer of salt thereof.

6. A compound of the formula (I) as claimed in claim 1 in which $R^1$ is hydrogen;

$R^2$ is ethyl or methoxymethyl;

$R^3$ is fluorine, chlorine, bromine, or methoxy;

A is N;

X is NH;

$R^4$ and $R^{4'}$ are hydrogen;

$R^5$ is $(C_1-C_2)$-alkyl, $(C_2-C_{20})$-alkenyl, $(C_2-C_{20})$-alkynyl, aryl or heterocyclyl, it being possible for the aryl or heterocyclyl radicals mentioned to be unsubstituted or having attached to them up to three, in the case of fluorine also up to the maximum number of, identical or different radicals and it being possible, in the alkyl, alkenyl or alkynyl radicals mentioned, for one or more non-adjacent saturated carbon units to be replaced by hetero atom units selected from the group consisting of $SiR^7R^8$, $R^7$ and $R^8$ being $(C_1-C_4)$,-alkyl and in which, moreover, 3 to 6 atoms of these hydrocarbon radicals which are optionally modified as above optionally form a cycle and these hydrocarbon radicals, with or without the variations mentioned, are optionally substituted by one or more, in the case of halogen up to the maximum number of, identical or different radicals selected from the group consisting of halogen, aryl, aryloxy, arylthio, $(C_3-C_8)$-cycloalkoxy, $(C_3-C_8)$-cycloalkylthio, heterocyclyl, heterocyclyloxy to $(C_1-C_2)$-alkoxycarbonyl, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents;

or a tautomer or salt thereof.

7. A compound of the formula (I) as claimed in claim 1 in which $R^5$ is $(C_1-C_{15})$-alkyl, aryl or heterocyclyl in the sense of a heteroaromatic ring system, it being possible for the aryl or heterocyclyl radical to be unsubstituted or to have attached to it up to three, in the case of fluorine also up to the maximum number of, identical or different radicals and it being possible, in the alkyl radical mentioned, for one or more non-adjacent saturated carbon units to be replaced by oxygen, and in which, moreover, 3 to 8 atoms of this alkyl radical which is optionally modified as above optionally form a cycle and this alkyl radical, with or without the variations mentioned, is optionally be substituted by one or more halogen atoms, in the case of fluorine also up to the maximum number, or with an aryl radical, and this aryl radical is be unsubstituted or have attached to it up to three, in the case of fluorine also up to the maximum number of, identical or different substituents;

or a tautomer or salt thereof.

8. A compound of the formula I in claim 1 in which the hetero atom unit in $R^2$ and $R^3$ is oxygen, $S(O)_x$, where x is 0, 1 or 2 and the hetero atom unit in $R^5$ is oxygen, $S(O)_x$, where x is 0, 1 or 2, $NR^6$ or $SiR^7R^8$, where $R^6$ is hydrogen, $(C_1-C_4)$-alkyl, $(C_1-C_4)$-alkoxy, $(C_1-C_4)$-alkanoyl and $R^7$ and $R^8$ are $(C_1-C_4)$-alkyl.

9. A composition comprising at least one compound as claimed in claim 1 and at least one formulation auxiliary.

10. A fungicidal composition comprising a fungicidally active amount of at least one compound as claimed in claim 1 together with the additives or auxiliaries conventionally used for this application.

11. An insecticidal, acaricidal, ixodicidal or nematicidal composition comprising an effective amount of at least one compound as claimed in claim 1 together with the additives or auxiliaries conventionally used for this application.

12. A crop protection product comprising a fungicidally, insecticidally, acaricidally or nematicidally effective amount of at least one compound as claimed in claim 1 and at least one further active substance from the series of the fungicides, insecticides, attractants, sterilants, acaricides, nematicides and herbicides together with the auxiliaries and additives conventionally used for this application.

13. A composition for use in timber protection or as preservative in sealants, in paints, in cooling lubricants for metal working or in drilling and cutting oils, comprising an effective amount of at least one compound as claimed in claim 1 together with the auxiliaries or additives conventionally used for this application.

14. A method of controlling phytopathogenic fungi, which comprises applying a fungicidally effective amount of a compound as defined in formula (1) in claim 1 or a composition as defined in claim 10 to these phytopathogenic fungi or to the plants, areas or substrates infected with them, or to seed.

15. A method for controlling harmful insects, Acarina, mollusks and nematodes in which an effective amount of a compound as defined in formula (I) in claim 1 or a composition as defined in claim 10 is applied to these harmful insects, Acarina, mollusks and nematodes or to the plants, areas or substrates infested with them.

16. Seed, treated or coated with an effective amount of a compound as defined in formula (I) in claim 1 or a composition as defined in claim 9.

* * * * *